(12) United States Patent
Zemlok et al.

(10) Patent No.: US 9,782,170 B2
(45) Date of Patent: Oct. 10, 2017

(54) SURGICAL STAPLING APPARATUS

(71) Applicant: Covidien LP, Mansfield, MA (US)

(72) Inventors: Michael A. Zemlok, Prospect, CT (US); Adam Ross, Prospect, CT (US); Russell Pribanic, Roxbury, CT (US); Ryan Williams, New Hartford, CT (US)

(73) Assignee: Covidien LP, Mansfield, MA (US)

( * ) Notice: Subject to any disclaimer, the term of this patent is extended or adjusted under 35 U.S.C. 154(b) by 381 days.

(21) Appl. No.: 14/598,684

(22) Filed: Jan. 16, 2015

(65) Prior Publication Data

US 2015/0122871 A1    May 7, 2015

Related U.S. Application Data

(63) Continuation of application No. 13/423,545, filed on Mar. 19, 2012, now Pat. No. 8,955,732, which is a
(Continued)

(51) Int. Cl.
*A61B 17/04* (2006.01)
*A61B 17/10* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC   A61B 2017/07278; A61B 2017/07264; A61B 2017/07257; A61B 2019/465; A61B 2019/4857; A61B 17/00022; A61B 17/068
(Continued)

(56) References Cited

U.S. PATENT DOCUMENTS

| 4,475,679 | A | | 10/1984 | Fleury, Jr. |
| 4,485,816 | A | | 12/1984 | Krumme |
| 4,550,870 | A | * | 11/1985 | Krumme .............. A61B 17/072 227/120 |

(Continued)

FOREIGN PATENT DOCUMENTS

| EP | 1728475 A2 | 12/2006 |
| EP | 1769756 A1 | 4/2007 |

(Continued)

OTHER PUBLICATIONS

Canadian Office Action issued in corresponding Canadian Appln. No. 2,709,777 dated May 12, 2016.
(Continued)

*Primary Examiner* — Robert Long

(57) ABSTRACT

A surgical stapling apparatus is provided and includes a housing, an elongated member, an end effector, and a staple formation circuit. The elongated member extends from the housing. The end effector is disposed on an end of the elongated member and has first and second jaws. The first jaw includes a staple cartridge having a plurality of staples. Each of the staples has first and second legs. The second jaw has a plurality of staple forming pockets. The staple formation circuit may be disposed on the second jaw. The staple formation circuit communicates a signal to a controller coupled to the staple formation circuit. The signal is representative of one or more of a formation, a malformation, and a nonformation of one or both of the first and second legs of one or more of the staples within one or more of the staple forming pockets.

19 Claims, 30 Drawing Sheets

Related U.S. Application Data continuation-in-part of application No. 13/025,262, filed on Feb. 11, 2011, now Pat. No. 8,276,801, which is a continuation-in-part of application No. 13/018,467, filed on Feb. 1, 2011, now abandoned, which is a continuation-in-part of application No. 12/796,270, filed on Jun. 8, 2010, now Pat. No. 8,360,299.

(60) Provisional application No. 61/232,806, filed on Aug. 11, 2009.

(51) Int. Cl.
    *A61B 17/068* (2006.01)
    *A61B 17/072* (2006.01)
    *A61B 90/90* (2016.01)
    *A61B 17/00* (2006.01)
    *A61B 90/00* (2016.01)

(52) U.S. Cl.
    CPC .... *A61B 90/90* (2016.02); *A61B 2017/00022* (2013.01); *A61B 2017/00115* (2013.01); *A61B 2017/00123* (2013.01); *A61B 2017/00221* (2013.01); *A61B 2017/00398* (2013.01); *A61B 2017/00473* (2013.01); *A61B 2017/00477* (2013.01); *A61B 2017/00685* (2013.01); *A61B 2017/00845* (2013.01); *A61B 2017/00853* (2013.01); *A61B 2017/07221* (2013.01); *A61B 2017/07257* (2013.01); *A61B 2017/07271* (2013.01); *A61B 2017/07278* (2013.01); *A61B 2090/065* (2016.02); *A61B 2090/0811* (2016.02)

(58) Field of Classification Search
    USPC ............ 227/175.1–182.1; 606/219–221
    See application file for complete search history.

(56) References Cited

U.S. PATENT DOCUMENTS

| | | | |
|---|---|---|---|
| 5,258,007 A | 11/1993 | Spetzler et al. | |
| 5,389,098 A * | 2/1995 | Tsuruta | A61B 17/00234 606/142 |
| 5,503,320 A | 4/1996 | Webster et al. | |
| 5,518,164 A * | 5/1996 | Hooven | A61B 17/07207 227/176.1 |
| 5,526,822 A | 6/1996 | Burbank et al. | |
| 5,630,539 A | 5/1997 | Plyley et al. | |
| 5,639,007 A | 6/1997 | Nakamura | |
| 5,685,474 A | 11/1997 | Seeber | |
| 5,833,695 A | 11/1998 | Yoon | |
| 5,876,401 A | 3/1999 | Schulze et al. | |
| 5,894,979 A | 4/1999 | Powell | |
| 5,992,724 A * | 11/1999 | Snyder | B25C 5/1689 227/120 |
| H001904 H * | 10/2000 | Yates | A61B 17/07207 606/142 |
| H002037 H * | 7/2002 | Yates | A61B 17/07207 606/51 |
| 6,817,508 B1 | 11/2004 | Racenet et al. | |
| 6,830,174 B2 | 12/2004 | Hillstead et al. | |
| 6,978,921 B2 | 12/2005 | Shelton, IV et al. | |
| 7,140,528 B2 | 11/2006 | Shelton, IV | |
| 7,182,239 B1 | 2/2007 | Myers | |
| 7,237,708 B1 | 7/2007 | Guy et al. | |
| 7,448,525 B2 | 11/2008 | Shelton, IV et al. | |
| 7,506,790 B2 | 3/2009 | Shelton, IV | |
| 7,559,452 B2 | 7/2009 | Wales et al. | |
| 7,559,453 B2 * | 7/2009 | Heinrich | A61B 17/072 227/175.1 |
| 7,673,780 B2 | 3/2010 | Shelton, IV et al. | |
| 7,717,312 B2 | 5/2010 | Beetel | |
| 7,784,663 B2 | 8/2010 | Shelton, IV | |
| 8,276,801 B2 | 10/2012 | Zemlok et al. | |
| 8,360,299 B2 | 1/2013 | Zemlok et al. | |
| 8,544,711 B2 | 10/2013 | Ma et al. | |
| 8,627,994 B2 | 1/2014 | Zemlok et al. | |
| 8,636,190 B2 | 1/2014 | Zemlok et al. | |
| 8,955,732 B2 | 2/2015 | Zemlok et al. | |
| 9,220,502 B2 * | 12/2015 | Zemlok | A61B 17/07207 |
| 2003/0036755 A1 | 2/2003 | Ginn | |
| 2003/0099102 A1 | 5/2003 | Duval | |
| 2003/0130677 A1 | 7/2003 | Whitman et al. | |
| 2004/0254608 A1 | 12/2004 | Huitema et al. | |
| 2005/0070958 A1 | 3/2005 | Swayze et al. | |
| 2005/0131390 A1 | 6/2005 | Heinrich et al. | |
| 2005/0184121 A1 * | 8/2005 | Heinrich | A61B 17/0686 227/175.1 |
| 2005/0203547 A1 | 9/2005 | Weller et al. | |
| 2006/0124688 A1 | 6/2006 | Racenet et al. | |
| 2006/0212069 A1 | 9/2006 | Shelton | |
| 2006/0231583 A1 * | 10/2006 | Kumayama | B25C 5/1603 227/134 |
| 2006/0271094 A1 | 11/2006 | Hudson et al. | |
| 2006/0273135 A1 | 12/2006 | Beetel | |
| 2006/0289600 A1 | 12/2006 | Wales et al. | |
| 2006/0291981 A1 | 12/2006 | Viola et al. | |
| 2007/0027469 A1 * | 2/2007 | Smith | A61B 17/07207 606/205 |
| 2007/0102472 A1 * | 5/2007 | Shelton | A61B 17/07207 227/175.1 |
| 2007/0179408 A1 | 8/2007 | Soltz | |
| 2007/0233161 A1 | 10/2007 | Weller et al. | |
| 2008/0283571 A1 | 11/2008 | Boyden et al. | |
| 2008/0312687 A1 * | 12/2008 | Blier | A61B 17/0644 606/219 |
| 2009/0054908 A1 * | 2/2009 | Zand | A61B 5/0071 606/130 |
| 2009/0076534 A1 | 3/2009 | Shelton, IV et al. | |
| 2009/0090763 A1 | 4/2009 | Zemlok et al. | |
| 2009/0209990 A1 | 8/2009 | Yates et al. | |
| 2009/0234248 A1 | 9/2009 | Zand et al. | |
| 2009/0261144 A1 | 10/2009 | Sniffin et al. | |
| 2009/0318957 A1 | 12/2009 | Viola et al. | |
| 2010/0096435 A1 * | 4/2010 | Fuchs | A61B 17/1114 227/179.1 |
| 2010/0200637 A1 | 8/2010 | Beetel | |
| 2011/0022032 A1 | 1/2011 | Zemlok et al. | |
| 2011/0155781 A1 | 6/2011 | Swensgard et al. | |
| 2011/0309128 A1 * | 12/2011 | Okoniewski | A61B 17/07207 227/176.1 |
| 2012/0228358 A1 * | 9/2012 | Zemlok | A61B 17/072 227/176.1 |
| 2013/0008935 A1 * | 1/2013 | Brusaw | B25C 5/0207 227/4 |
| 2013/0168431 A1 * | 7/2013 | Zemlok | A61B 17/07207 227/175.1 |
| 2014/0252063 A1 | 9/2014 | Ross et al. | |

FOREIGN PATENT DOCUMENTS

| | | |
|---|---|---|
| EP | 1796754 A2 | 6/2007 |
| EP | 1 813 206 A1 | 8/2007 |
| EP | 1813201 A1 | 8/2007 |
| EP | 1997438 | 12/2008 |
| EP | 2277458 A1 | 1/2011 |
| JP | H05-337119 A | 12/1993 |
| JP | 2006-334417 A | 12/2006 |
| WO | 98/30153 A1 | 7/1998 |
| WO | 02/30296 A2 | 4/2002 |
| WO | 03/026511 A1 | 4/2003 |
| WO | 03/049906 A1 | 6/2003 |
| WO | 03/090630 A3 | 4/2004 |
| WO | 2010-088044 A2 | 8/2010 |

OTHER PUBLICATIONS

European Search Report for corresponding EP 10 25 1415, date of completion is Sep. 22, 2010 (3 pages).

(56) References Cited

OTHER PUBLICATIONS

European Search Report from corresponding European Application No. EP 10 25 1306 dated of completion Dec. 2, 2010.
European Search Report for corresponding EP 08 25 1988.5; completed Sep. 19, 2008; mailed Oct. 17, 2008; 3 pages.
European Search Report dated Jul. 28, 2011 for EP 11 15 2266.
European Search Report for EP 12154611.3 date of completion is Aug. 1, 2012 (10 pages).
Australian Examination Report issued in corresponding Australian Appln. No. 2013206692 dated May 19, 2016.
European Search Report issued in corresponding European Application No. EP 15185132 dated Jan. 20, 2016.
Japanese Office Action corresponding to Japanese Application No. 2012-017921 mailed Sep. 29, 2015.
Japanese Office Action issued in corresponding Japanese Application No. 2015-246920 dated Mar. 27, 2017.
European Examination Report issued in European Application No. 15185132.6 dated May 26, 2017.
Japanese Notice of Allowance issued in Japanese Application No. 2015-246920 dated Aug. 3, 2017.

* cited by examiner

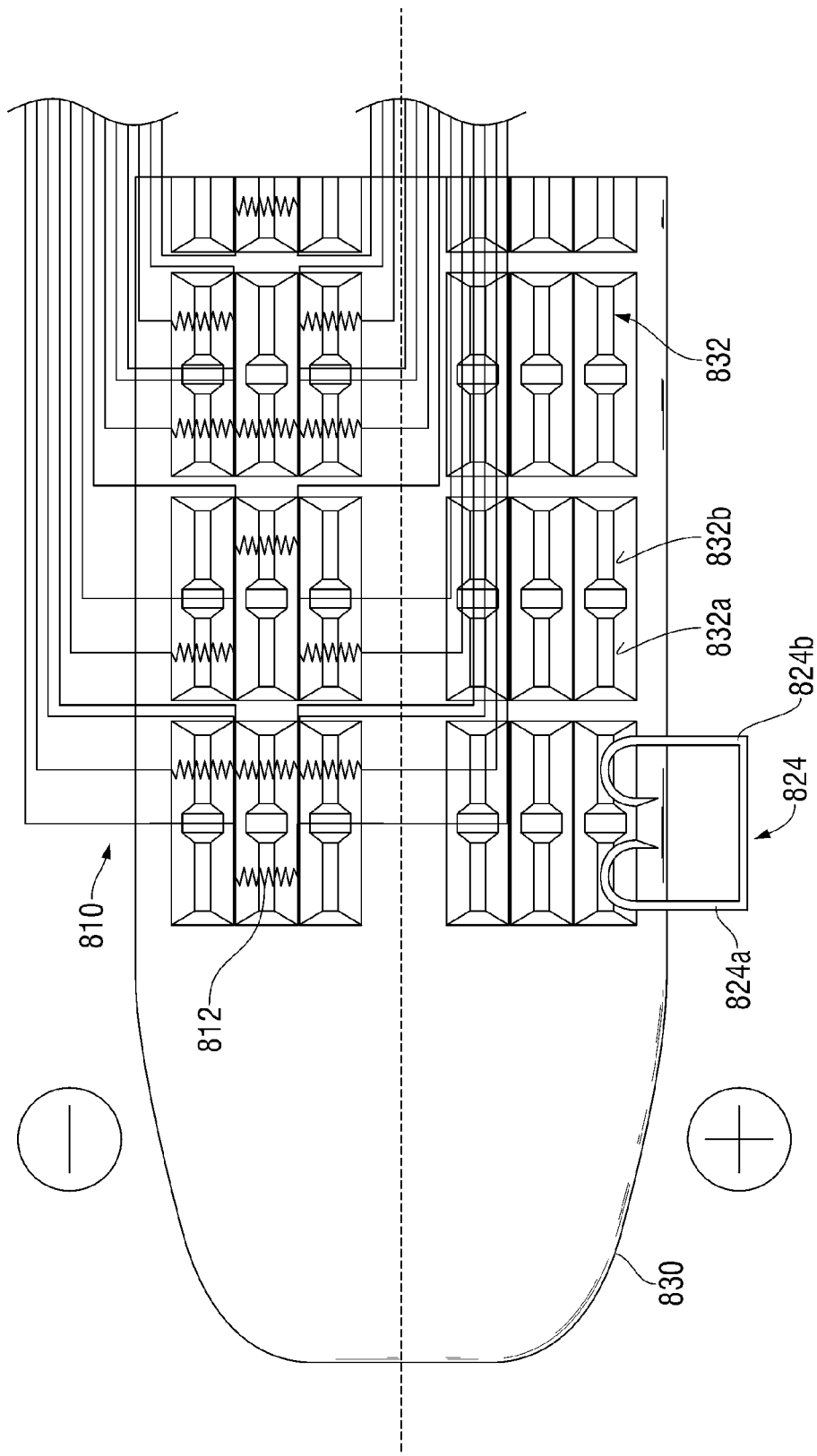

SURGICAL STAPLING APPARATUS

CROSS REFERENCE TO RELATED APPLICATIONS

The present application is a continuation of U.S. patent application Ser. No. 13/423,545, filed Mar. 19, 2012, which is a Continuation-in-Part application which claims priority to, and the benefit of U.S. patent application Ser. No. 13/025,262, filed on Feb. 11, 2011, now U.S. Pat. No. 8,276,801, which is a Continuation-in-Part application which claims priority to, and the benefit of U.S. patent application Ser. No. 13/018,467 filed on Feb. 1, 2011, now abandoned, which is a Continuation-in-Part application which claims priority to, and the benefit of U.S. patent application Ser. No. 12/796,270, filed on Jun. 8, 2010, now U.S. Pat. No. 8,360,299, which claims priority to, and the benefit of U.S. Provisional Application Ser. No. 61/232,826, filed on Aug. 11, 2009, the entire contents of each of which are incorporated herein by reference.

BACKGROUND

1. Technical Field

The present disclosure relates to surgical stapling apparatuses that are capable of applying lines of fasteners to tissue while cutting the tissue between those fastener lines and, more particularly, to improvements relating to fastener deployment and formation.

2. Background of Related Art

Endoscopic and laparoscopic surgical apparatuses are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to access organs, tissues and/or vessels far removed from the incision. Thus, apparatuses used in such procedures are typically long and narrow while being functionally controllable from a proximal end of the apparatus.

Significant development has gone into a range of endoscopic surgical apparatuses that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical stapling apparatuses include an end effector that applies lines of fasteners. The end effector includes a pair of cooperating jaws that, if the apparatus is intended for endoscopic or laparoscopic applications, are capable of passing through a cannula passageway. One of the jaws receives a fastener cartridge having at least two spaced rows of fasteners (e.g., staples). The other jaw defines an anvil having fastener-forming pockets aligned with the rows of fasteners in the cartridge. The apparatus includes a plurality of reciprocating wedges or cam bars which, when driven, pass through openings in the fastener cartridge and engage drivers supporting the fasteners to effect the firing of the fasteners toward the anvil.

Small videoscopes of various types (e.g., endoscopes) may be relied upon to monitor proper positioning and operation of the surgical stapling apparatus. While effective to a degree, it is desirable to have improved monitoring of operation of the surgical stapling apparatus. When utilizing stapling devices containing multiple fasteners in each cartridge load, it is also beneficial to determine which fasteners are being deployed and whether they are being formed properly.

More particularly, during surgical stapling procedures it is beneficial to have verification that the fasteners are forming properly because it promotes seal integrity and the mechanical strength of the connected tissues. The need for this recognition is of greater importance when the tissue is also being transacted with a knife blade along the side or between the fastener line to give the surgeon additional confidence that excessive bleeding and/or contamination is not taking place.

Consequently, a continuing need exists for an improved surgical stapling and severing apparatus that incorporates fastener deployment and formation monitoring capabilities to assure the mechanical and hemostatic integrity of a surgical stapling device.

SUMMARY

In accordance with the present disclosure, a surgical stapling apparatus is disclosed. The surgical stapling apparatus has a housing having an actuator; an elongated member extending from the housing; an end effector disposed on one end of the elongated member, the end effector including first and second jaws; a plurality of fasteners disposed in the end effector; a plurality of pusher members located in the end effector, each pusher member in the plurality of pusher members operatively coupled to a number of fasteners; an actuation mechanism operatively coupled to the actuator, the actuation mechanism including a longitudinally translatable drive member and an actuation sled coupled thereto, the actuation sled configured for engaging the plurality of pusher members; and a pressure responsive element disposed in one of the jaws, the pressure responsive element communicating a signal to a controller coupled to the surgical stapling apparatus, the signal representative of pressure applied to the pressure responsive element.

In one embodiment, interaction between the actuation sled and the pusher members applies pressure to the pressure responsive element. The pressure responsive element includes staggered pressure sensors in a circuit. The circuit, in some manifestations is a printed pressure circuit or a flexible circuit disposed on the surface of a channel positioned in one of the jaws.

In another embodiment, the surgical stapling apparatus can include a circuit that is disposed on the external surface of at least one of the jaws. In this version, the stapling apparatus also includes a beam, the beam disposed on the external surface of at least one of the jaws and seated in a groove disposed within at least one of the jaws so that the beam can be configured to translate along the groove. The beam may be an I-beam or an E-beam.

The circuit can have a laminate layer on the circuit and may even have a lubricant coating on the laminate layer. The signal communicated to the controller will from time to time be read by the controller as irregular. In such a case, the controller will activate a feedback response such as an error code, warning, or it may even stop fastener deployment altogether. It is contemplated that the pressure responsive element communicates the signal to the controller through by any of the following: voltage, resistance, impedance, electromagnetism, radio frequency, current, inductance, capacitance, infrared, optics, or any combination thereof.

Another embodiment envisions a knife configured to translate through the jaw to cut tissue. However, upon certain predetermined irregularities, the controller can prevent the knife from cutting, should those irregularities fall within those predetermined conditions. An encoder is configured to recognize irregular component positions relative to the pressure applied and send a signal to the controller. The encoder may be configured to recognize irregular positions of various components including the actuation mechanism, the knife, the actuator, the actuation sled, the pusher member, the first jaw, the second jaw, or even various combinations thereof. These encoders can be linear or rotational.

Certain embodiments contemplate the circuit including a cartridge identifying feature. Other embodiments can have controller configured to set positional limitations and run mode for a particular load or fastener type. Still further, one of the jaws may be configured and dimensioned to house a non-linear cartridge.

In other embodiments, the controller includes an end user feedback communication feature. The end user feedback communication feature is configured to communicate the feedback to an end user through percipient signals such as audible, visual, tactile, or any combination thereof.

According to another aspect of the present disclosure, a surgical stapling apparatus is provided and includes a housing having an actuator; an elongated member extending from the housing; an end effector disposed on an end of the elongated member, the end effector having a first jaw and a second jaw, the first jaw having a staple cartridge and the second jaw having a plurality of staple forming recesses; the staple cartridge having at least a first segment and a second segment, the first segment and the second segment each having a tissue contacting surface and staple receiving slots defined in the tissue contacting surface, the first segment and the second segment being biased toward the second jaw and movable; a biasing members for each of the first segment and the second segment; and a pressure sensor for each of the first segment and the second segment.

The surgical stapling apparatus may further include a component for determining when the pressure is above a threshold value.

The surgical stapling apparatus may further include a motor operatively connected to the actuator. The motor may be in the housing.

The surgical stapling apparatus may further include a power source in the housing and operatively connected to the motor.

The component may be programmed to stop the motor.

The staple forming recesses and the staple receiving slots may define linear rows. The linear rows may extend transversely with respect to a longitudinal axis of the elongated member. The staple forming recesses and the staple receiving slots may define an angle with respect to a longitudinal axis of the end effector.

According to a further aspect of the present disclosure, an end effector for selective connection to a surgical apparatus, is provided and includes a first jaw; a staple cartridge supported on the first jaw, the staple cartridge defining a tissue contacting surface, wherein the staple cartridge is divided into a plurality of independent, separately movable segments, and at least one staple retaining slot is defined in each segment; a second jaw connected to the first jaw, the second jaw supporting an anvil, the anvil defining a plurality of staple forming recesses arranged in juxtaposed correspondence with the plurality of staple retaining slots of the staple cartridge; and a pressure sensing element interposed between each staple cartridge segment and the first jaw, wherein each pressure sensing element senses a force exerted on each respective staple cartridge segment.

The end effector may further include a biasing member interposed between each staple cartridge segment and the first jaw. The biasing members may maintain each staple cartridge segment spaced a distance from the first jaw.

The staple cartridge may define at least two parallel rows of staple retaining slots. At least one substantially adjacent staple retaining slot from each row of staple retaining slots may be provided in each staple cartridge segment.

The biasing members may compress upon exertion of a force on the tissue contacting surface of any of the staple cartridge segments.

According to still another aspect of the present disclosure, an electro-surgical stapling system is provided and includes a powered surgical apparatus and an end effector. The powered surgical apparatus includes a handle portion configured and adapted to releasably connect a surgical stapling end effector thereto, the handle portion including an actuator for connection to the end effector and for driving the end effector, a motor for driving the actuator, a power source for powering the motor, and a controller for controlling at least one of the power source and the motor. The end effector is configured for selective connection to the handle portion of the powered surgical apparatus. The end effector includes a first jaw; a staple cartridge supported on the first jaw, the staple cartridge defining a tissue contacting surface, wherein the staple cartridge is divided into a plurality of independent, separately movable segments, and at least one staple retaining slot is defined in each segment; a second jaw connected to the first jaw, the second jaw supporting an anvil, the anvil defining a plurality of staple forming recesses arranged in juxtaposed correspondence with the plurality of staple retaining slots of the staple cartridge; and a pressure sensing element interposed between each staple cartridge segment and the first jaw, wherein each pressure sensing element senses a force exerted on each respective staple cartridge segment. Each pressure sensing element is in electrical communication with the controller. The controller stops at least one of approximation of the first jaw and the second jaw, and firing of the powered surgical apparatus when a force exerted on at least one of the staple cartridge segments and sensed by the respective pressure sensing elements exceeds a predetermined threshold force.

The end effector may further include a biasing member interposed between each staple cartridge segment and the first jaw. The biasing members may maintain each staple cartridge segment spaced a distance from the first jaw.

The staple cartridge of the end effector may define at least two parallel rows of staple retaining slots. At least one substantially adjacent staple retaining slot from each row of staple retaining slots may be provided in each staple cartridge segment.

The biasing members of the end effector may compress upon exertion of a force on the tissue contacting surface of any of the staple cartridge segments.

The first jaw and the second jaw of the end effector may be configured for parallel approximation.

According to yet another aspect of the present disclosure, a surgical stapling apparatus is provided and includes a housing, an elongated member, an end effector, a staple formation circuit, and an energy source. The elongated member extends from the housing. The end effector is disposed on an end of the elongated member and has a first jaw and a second jaw. The first jaw includes a staple cartridge having a plurality of staples. Each of the staples has a first leg and a second leg. The second jaw has a plurality of staple forming pockets. The staple formation circuit may be at least partially disposed on the second jaw. The second jaw may include an electrically resistive material that electrically isolates at least a portion of the staple formation circuit and/or an electrically resistive material may electrically isolate the entire staple formation circuit. The staple formation circuit communicates a signal to a controller coupled to the staple formation circuit. The signal is representative of one or more of a formation, a malformation, and a nonformation of one or more of the first leg and the second leg of one or more of the staples of the plurality of staples within one or more of the staple forming pockets. The first and second legs of one or more of the staples of the plurality of staples may be monitored by the controller independently of the other leg. In response to the signal, the controller communicates a second signal and/or an output signal to the surgical stapling apparatus directing the surgical stapling apparatus to perform one or more operations. The one or more operations include one or more of preventing further staple formation, facilitating further staple formation, emitting a warning, and emitting an error feedback. The staple formation circuit may be configured in one or both of a parallel and a series circuit. The energy source is in electrical communication with the staple formation circuit and provides one or both of a voltage potential and a voltage waveform. The voltage potential or the voltage waveform may be in a microelectronic range.

One or more of the staple forming pockets may include a conductive pad in electrical communication with the staple formation circuit. The conductive pad forms an open loop circuit in the staple formation circuit. In this regard, the staple, upon formation, closes the open loop circuit, forming a closed loop circuit.

The staple formation circuit may include one or more electrical traces disposed within one or more of the staple forming pockets. The staple formation circuit may be a dual or single wire isolated circuit. The second jaw may be a common ground when the staple formation circuit is a single wire isolated circuit. The staple formation circuit may include a plurality of electrical traces positioned on the second jaw and associated with a respective staple forming pocket. The plurality of electrical traces may be layered and separated by electrically resistive material.

One or more electrical traces may be positioned on a bottom surface of one of the staple forming pockets. Each electrical trace may be electrically isolated from any other electrical traces. One or more of the staple forming pockets may include two or more recesses and one or more electrical traces positioned within each recess of the one or more staple forming pockets. The one or more electrical traces are operably coupled to one or more of a resistor, an inductor, a capacitor, a Piezo-Electric Crystal, and a transducer. One or more of the plurality of staples is configured to interrupt the one or more electrical traces as the one or more staples are formed in the one or more staple forming pockets such that the interruption of the one or more electrical traces facilitates the communication of the signal to the controller. One or more of the first and second legs of one or more of the staples of the plurality of staples may be driven into the one or more electrical traces with sufficient force to break the one or more electrical traces.

The end effector may include one or more position indicating features configured to track movement progression of one or more movable features. The one or more position indicating features include one or more of an encoder, a micro-switch, a magnetic transducer, and a displacement transducer. The one or more movable features include one or both of a sled and a knife. The one or more movable features are movably positionable along one or both of the jaws of the end effector. The one or more position indicating features are configured to communicate a first positioning signal to the controller. The first positioning signal represents the position of the one or more movable features as the one or more movable features move along one or both of the jaws of the end effector. Each staple communicates a second positioning signal to the controller upon formation of the staple. The second positioning signal represents the position of the formed staple. The controller is configured to compare the relative positions of the formed staple and the one or more movable features based upon the first and second positioning signals.

According to one aspect, the present disclosure relates to an end effector for selective connection to a surgical apparatus. The end effector includes a first jaw, a staple cartridge, a second jaw, and a staple formation circuit. The staple cartridge is supported on the first jaw. The staple cartridge has a plurality of staples positioned within a plurality of staple retaining slots. Each of the staples has a first leg and a second leg. The second jaw is connected to the first jaw. The second jaw supports an anvil defining a plurality of staple forming pockets arranged in juxtaposed correspondence with the plurality of staple retaining slots of the staple cartridge. The staple formation circuit is disposed on the anvil of the second jaw. The staple formation circuit communicates a signal to a controller operably coupled to the staple formation circuit. The signal is representative of one or more of a formation, a malformation, and a nonformation of one or both of the first and second legs of one or more of the staples of the plurality of staples within one or more of the staple forming pockets.

According to another aspect, the present disclosure relates to an electro-surgical stapling system including a powered surgical apparatus. The power surgical apparatus includes an energy source, a handle portion, and a controller. The handle portion is configured to releasably connect a surgical stapling end effector thereto. The surgical stapling end effector is configured for selective connection to the handle portion of the powered surgical apparatus. The handle portion includes an actuator for connection to the end effector and for driving the end effector. The controller controls the energy source and the surgical stapling end effector.

The surgical stapling end effector includes a first jaw, a staple cartridge, a second jaw, and a staple formation circuit. The staple cartridge is supported on the first jaw. The staple cartridge has a plurality of staples positioned within a plurality of staple retaining slots. Each of the staples has a first leg and a second leg. The second jaw is connected to the first jaw. The second jaw supports an anvil. The anvil defines a plurality of staple forming pockets arranged in juxtaposed correspondence with the plurality of staple retaining slots of the staple cartridge. The staple formation circuit is disposed on the anvil of the second jaw. The staple formation circuit communicates a signal to the controller. The signal is representative of one or more of a formation, a malformation, and a nonformation of one or more of the first and second legs of one or more of the staples of the plurality of staples within one or more of the staple forming pockets.

According to a further aspect, a surgical stapling apparatus includes a housing and an elongated member extending from the housing. An end effector is disposed on an end of the elongated member. The end effector has a first jaw member and a second jaw member. The first jaw member includes a staple cartridge having a segmented staple guide, one or more pressure sensing elements, and a locking feature.

The segmented staple guide has a plurality of segments, each of which are movable between one or more loaded positions and an unloaded position. Each segment of the staple guide is movable between one or more loaded positions and an unloaded position. Each segment of the staple guide may be spring loaded at a set height in the unloaded position. One or more segments of the staple guide may approximate the pressure sensing element when tissue is disposed between the first and second jaw members. Each segment of the staple guide may compress to one of the one or more loaded positions when tissue is clamped between the first jaw member and the second jaw member. One or more segments of the staple guide may be independently movable relative to the other segments of the staple guide. Each segment of the staple guide may be laterally and longitudinally pivotable in a fixed position relative to the other segments.

The one or more pressure sensing elements are configured to identify differences in applied pressure along the staple guide in response to movement of one or more of the plurality of segments of the staple guide when tissue is disposed between the first and second jaw members to sense variations in tissue thickness along the staple guide. The pressure sensing element may be segmented. In this regard, each segment of the staple guide may correspond to a segment of the pressure sensing element. The pressure sensing element may include a film.

The locking feature is configured to limit movement of the plurality of segments of the staple guide.

The first jaw member includes a first angled portion and the segmented staple guide includes a second angled portion. The first and second angled portions are disposed in registration to maintain the segmented staple guide in a substantially fixed position relative to the first jaw member.

The staple cartridge includes a one-piece staple pusher that deploys a plurality of staples from the staple cartridge independent of the positioning of any of the segments of the staple guide.

The surgical stapling apparatus may include a controller in electrical communication with the pressure sensing element. The controller is configured to identify unsafe loads along the staple guide based upon a first signal transmitted from the pressure sensing element and generate a second signal to the surgical stapling apparatus to prevent firing and/or clamping of the surgical stapling apparatus when an unsafe load is identified by the controller.

According to one aspect, an end effector for selective connection to a surgical apparatus includes a first jaw, a second jaw, and a staple cartridge. The second jaw is connected to the first jaw and supports an anvil. The anvil defines a plurality of staple forming pockets. The first jaw supports one or more pressure sensing elements. The pressure sensing element may be segmented. The staple cartridge is also supported on the first jaw.

The staple cartridge includes a plurality of staples, a segmented staple guide, and a one-piece staple pusher. The plurality of staples is positioned within a plurality of staple retaining slots. The staple forming pockets of the anvil are arranged in juxtaposed correspondence with the plurality of staple retaining slots of the staple cartridge. The segmented staple guide includes a plurality of movable segments. One or more movable segments of the plurality of movable segments of the segmented staple guide are independently movable relative to the other movable segments of the plurality of movable segments of the segmented staple guide. The one or more pressure sensing elements of the first jaw are configured to identify differences in applied pressure along the segmented staple guide in response to movement of at least one of the plurality of movable segments. The first jaw may include a locking feature that limits movement of the one or more movable segments of the segmented staple guide.

The one-piece staple pusher deploys the plurality of staples from the plurality of staple retaining slots independent of the positioning of any of the movable segments of the plurality of movable segments.

According to another aspect, an electro-surgical stapling system includes a powered surgical apparatus. The powered surgical apparatus includes an energy source, a handle portion, and a controller. The handle portion is configured to releasably connect a surgical stapling end effector thereto. The handle portion includes an actuator for connection to the end effector and for driving the end effector. The controller controls the energy source and the surgical stapling end effector. The surgical stapling end effector is configured for selective connection to the handle portion of the powered surgical apparatus.

The surgical stapling end effector includes a first jaw, a second jaw, and a staple cartridge. The second jaw is connected to the first jaw and supports an anvil. The anvil defines a plurality of staple forming pockets. The first jaw supports one or more pressure sensing elements and includes a locking feature. The staple cartridge is also supported on the first jaw.

The staple cartridge includes a plurality of staples, a segmented staple guide, and a staple pusher. The plurality of staples is positioned within a plurality of staple retaining slots. The staple forming pockets of the anvil arranged in juxtaposed correspondence with the plurality of staple retaining slots of the staple cartridge. The segmented staple guide includes a plurality of movable segments. The one or more pressure sensing elements of the first jaw are configured to identify differences in applied pressure along the segmented staple guide in response to movement of at least one of the plurality of movable segments. The locking feature of the first jaw limits movement of the plurality of segments of the segmented staple guide. The staple pusher deploys the plurality of staples from the plurality of staple retaining slots independent of the positioning of any of the movable segments of the plurality of movable segments.

BRIEF DESCRIPTION OF THE DRAWINGS

The above and other aspects, features, and advantages of the present disclosure will become more apparent in light of the following detailed description when taken in conjunction with the accompanying drawings in which:

FIG. 18A is an enlarged, illustrative plan view of a portion of one embodiment of an anvil of the surgical stapling apparatus of FIG. 17 with a staple being shown formed in a staple forming pocket of the anvil;

DETAILED DESCRIPTION OF EMBODIMENTS

Figure 1A:
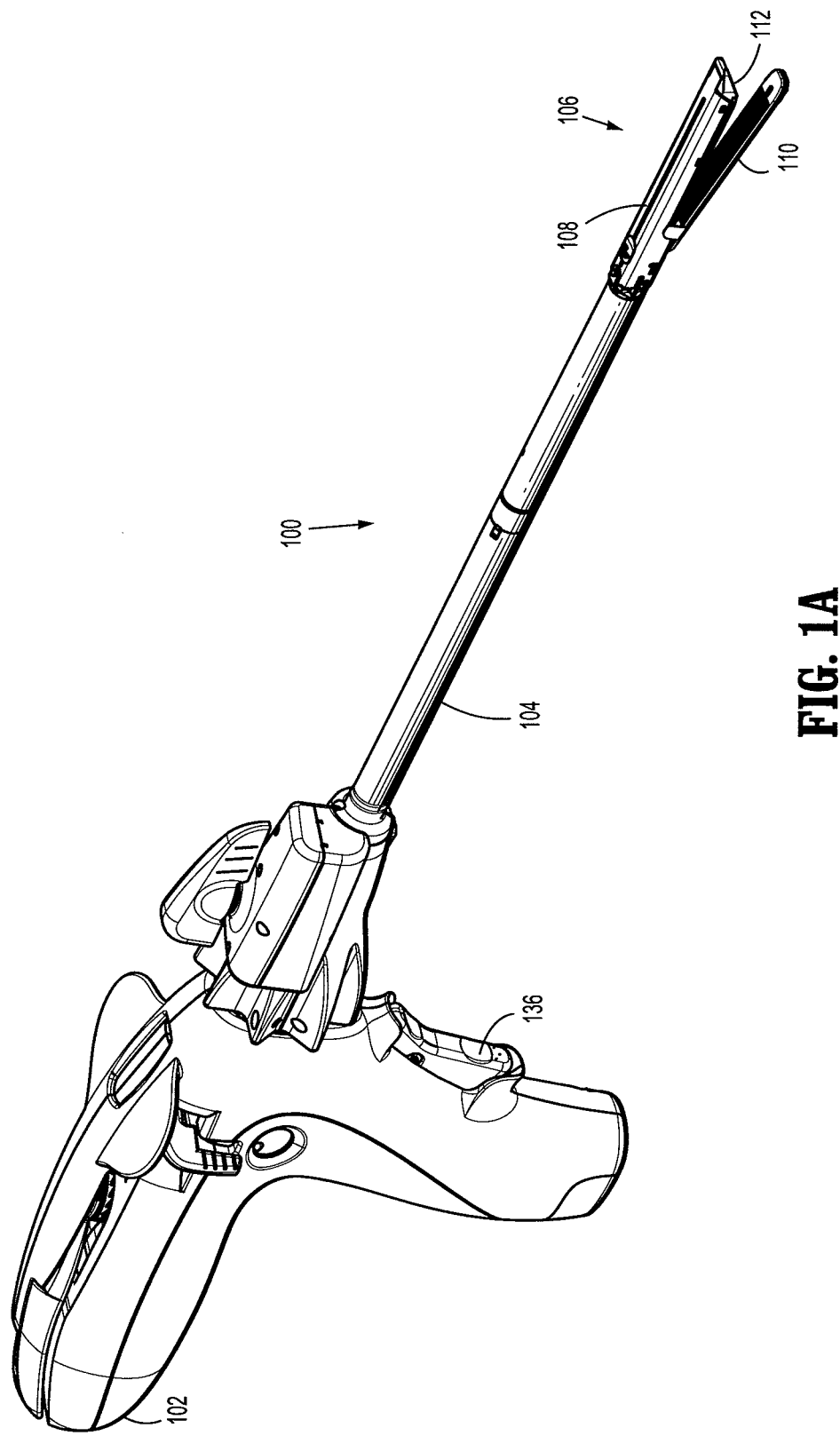
FIG. 1A is a perspective view of a powered surgical stapling apparatus.

Embodiments of the presently disclosed surgical stapling apparatus will now be described in detail with reference to the drawings, in which like reference numerals designate identical or corresponding elements in each of the several views.

As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Figure 1B:
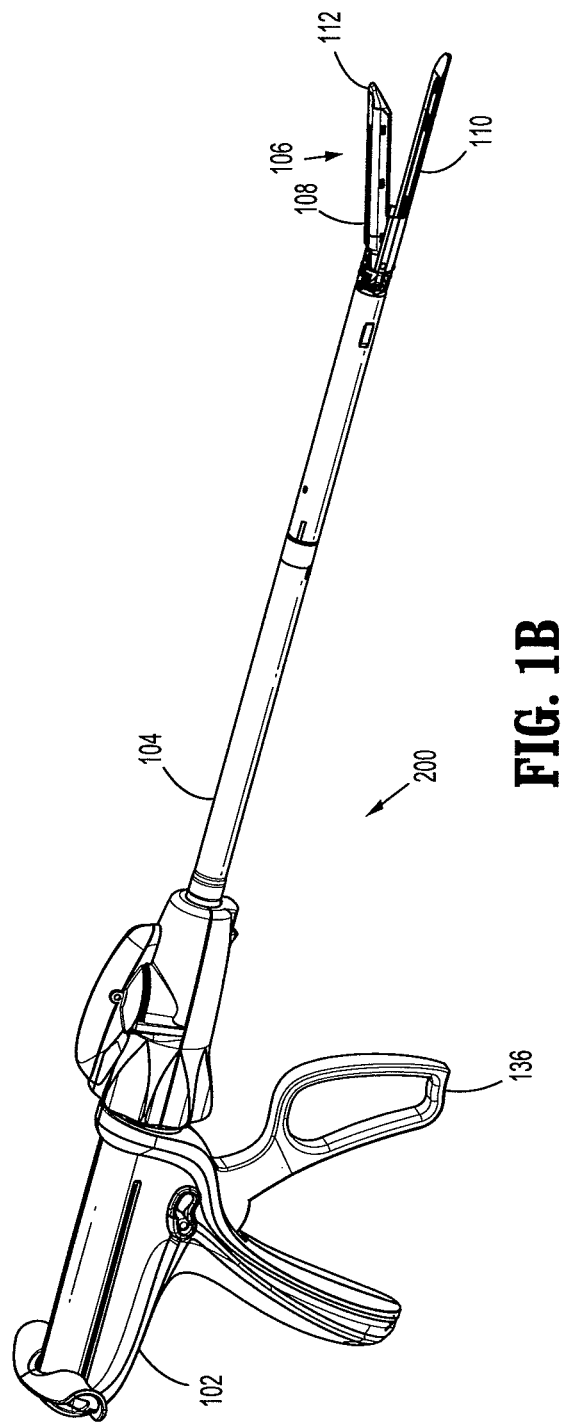
FIG. 1B is a perspective view of a manual surgical stapling apparatus.

FIG. 1A illustrates a powered surgical stapling apparatus shown generally as 100. FIG. 1B illustrates a manual surgical stapling apparatus shown generally as 200. Briefly, surgical stapling apparatus 100, 200 includes a housing 102 having an actuator 136, an elongated member 104 extending from housing 102, and an end effector 106 disposed on one end of elongated member 104. From FIGS. 1C-1D, end effector 106 includes first and second jaws 108, 110, a plurality of fasteners 114 disposed in end effector 106 and a plurality of pusher members 130 located in end effector 106. Each pusher member 130 in plurality of pusher members 130 is operatively coupled to a number of fasteners 114. As seen in FIGS. 3A-4B, surgical stapling apparatus 100, 200 includes an actuation mechanism 138 operatively coupled to actuator 136. Actuation mechanism 138 includes a longitudinally translatable drive member 140 and an actuation sled 132 coupled thereto. Actuation sled 132 is configured for engaging the plurality of pusher members 130.

Figure 1C:
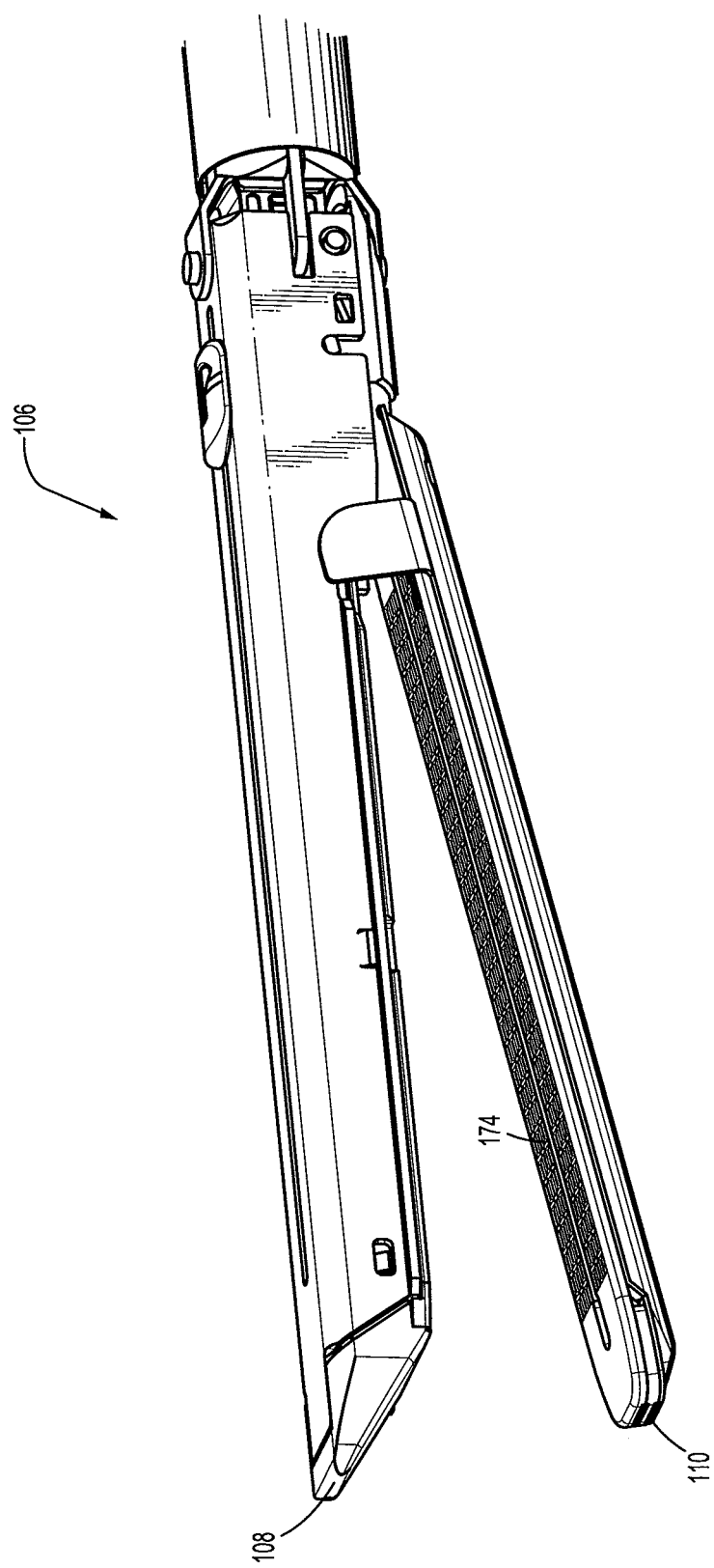
FIG. 1C is an enlarged perspective view of the end effector of a surgical stapling apparatus.
Figure 2:
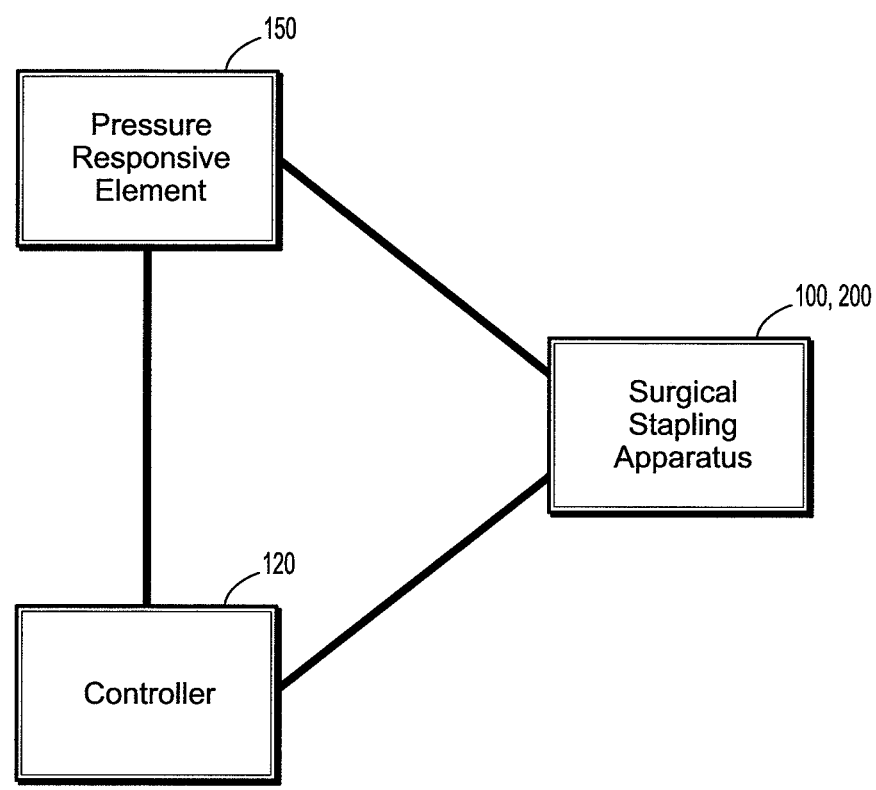
FIG. 2 is a block diagram of a surgical stapling system in accordance with the present disclosure.

In accordance with one embodiment of the present disclosure, FIG. 2 diagrams a surgical stapling system having a surgical stapling apparatus 100, 200, surgical stapling apparatus 100, 200 having a pressure responsive element 150 and a controller 120. It is envisioned that pressure responsive element is disposed in one of jaws 108, 110 (FIGS. 3A-3B and 8A-8B). Pressure responsive element 150 can communicate a pressure signal 152 (not shown) to controller 120 coupled to surgical stapling apparatus 100, 200. Controller 120 is a microcontroller or an analog circuit which enables control, positioning, status, and fastener 114 quality feedback. Pressure signal 152 is representative of pressure applied to pressure responsive element 150. It is envisioned that this embodiment may include a knife 164 or be knifeless, knife 164 slidably translatable through a knife slot 174 (FIG. 1C).

Figure 5:
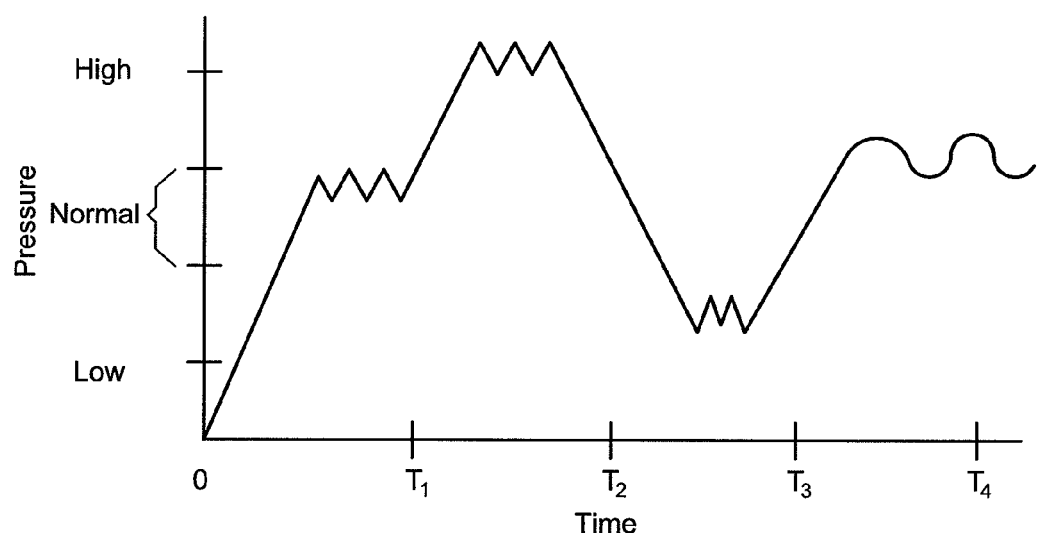
FIG. 5 is a plot of the pressure applied to form staples versus time.

Referring to FIG. 5, applied pressure may be measured in the form of waveform pulsations as seen in the time versus applied pressure graph. For example, a normal sample might read in accordance with the graph covering the time period from 0-t1. If the waveform pulsations indicate a low (t2-t3) or high (t1-t2) pressure during a certain sampling, this could be an indication that the fasteners 114 are not being properly deployed or formed due to improper applied pressure distribution necessary for proper fastener 114 deployment or formation. Alternatively, if the waveform is not a shape that has been correlated with successful test waveforms (t3-t4), an error code or feedback is initiated by the controller 120 to stop deployment or formation progression. This gives the end user the ability to properly understand the performance irregularity before proceeding or backing out.

Figure 3A:
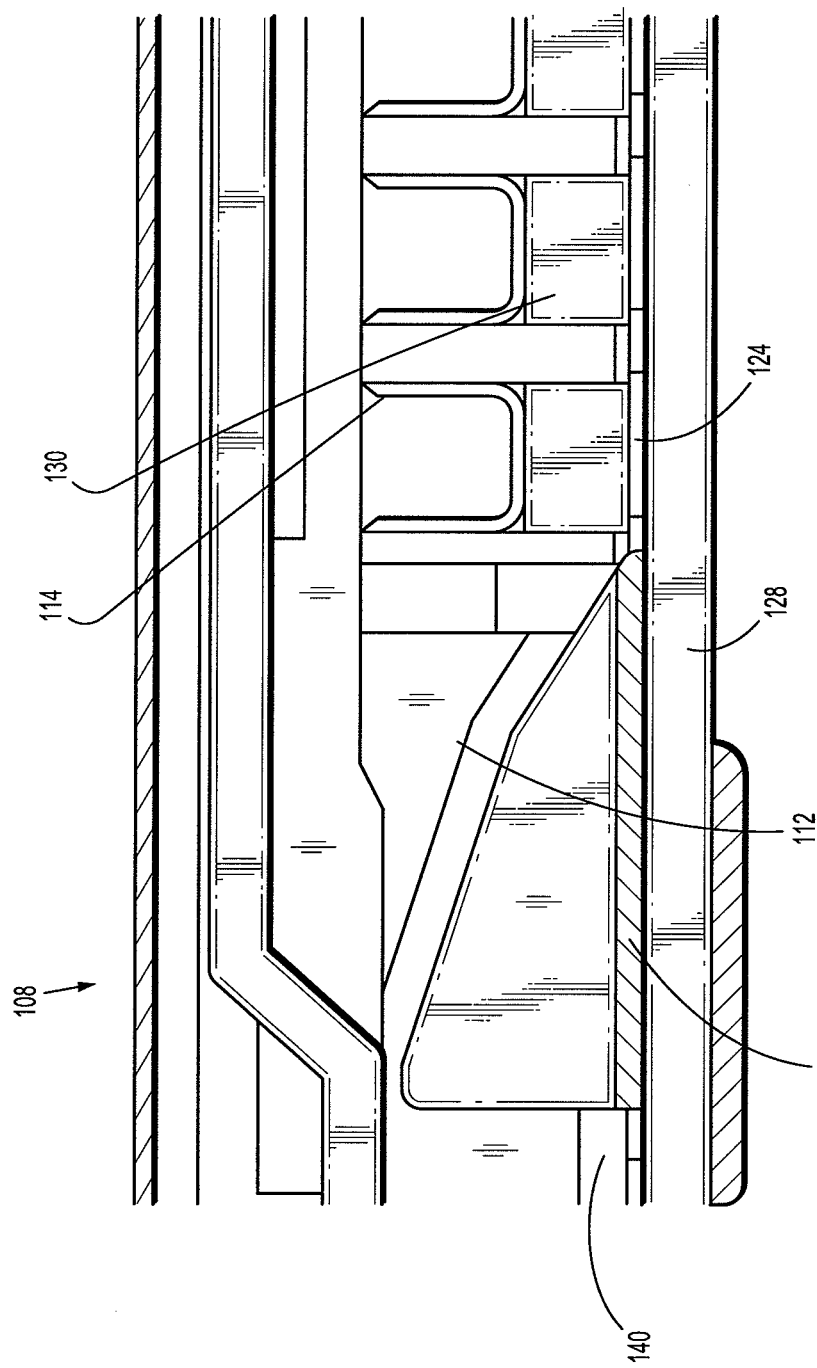
FIG. 3A is a side cross-sectional view of a portion of the end effector of the surgical stapling apparatus' of FIGS. 1A and 1B.
Figure 3B:
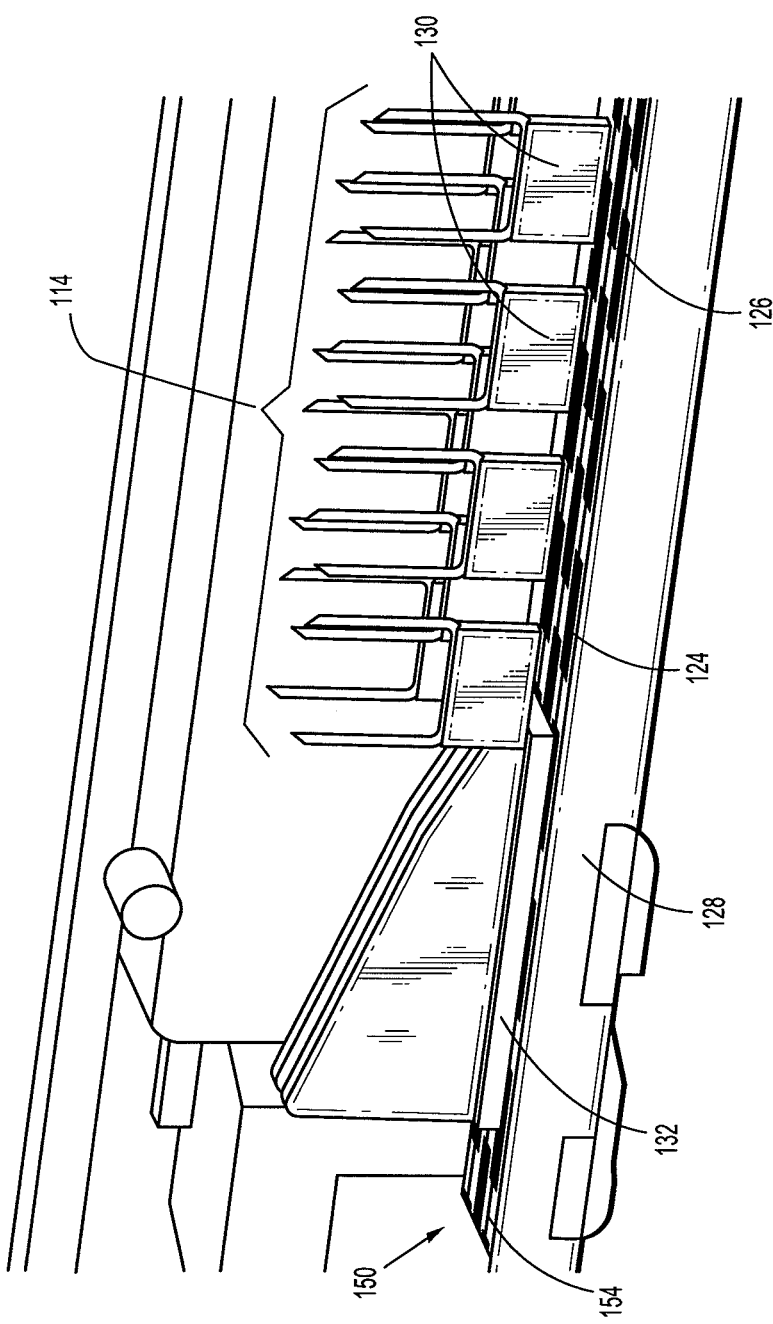
FIG. 3B is a side cross-sectional view of a portion of the end effector of the surgical stapling apparatus' of FIGS. 1A and 1B with a cartridge wall removed for clarity.

As seen in FIGS. 3A-3B, first jaw 108 includes a cartridge channel 128 for receiving a cartridge 112. Cartridge 112 includes a plurality of fasteners 114 disposed therein. Typically, fasteners 114 are in the form of a plurality of surgical staples. Cartridge 112 houses fasteners 114 in a plurality of linear rows, which are operatively coupled to pusher members 130.

Figure 6:
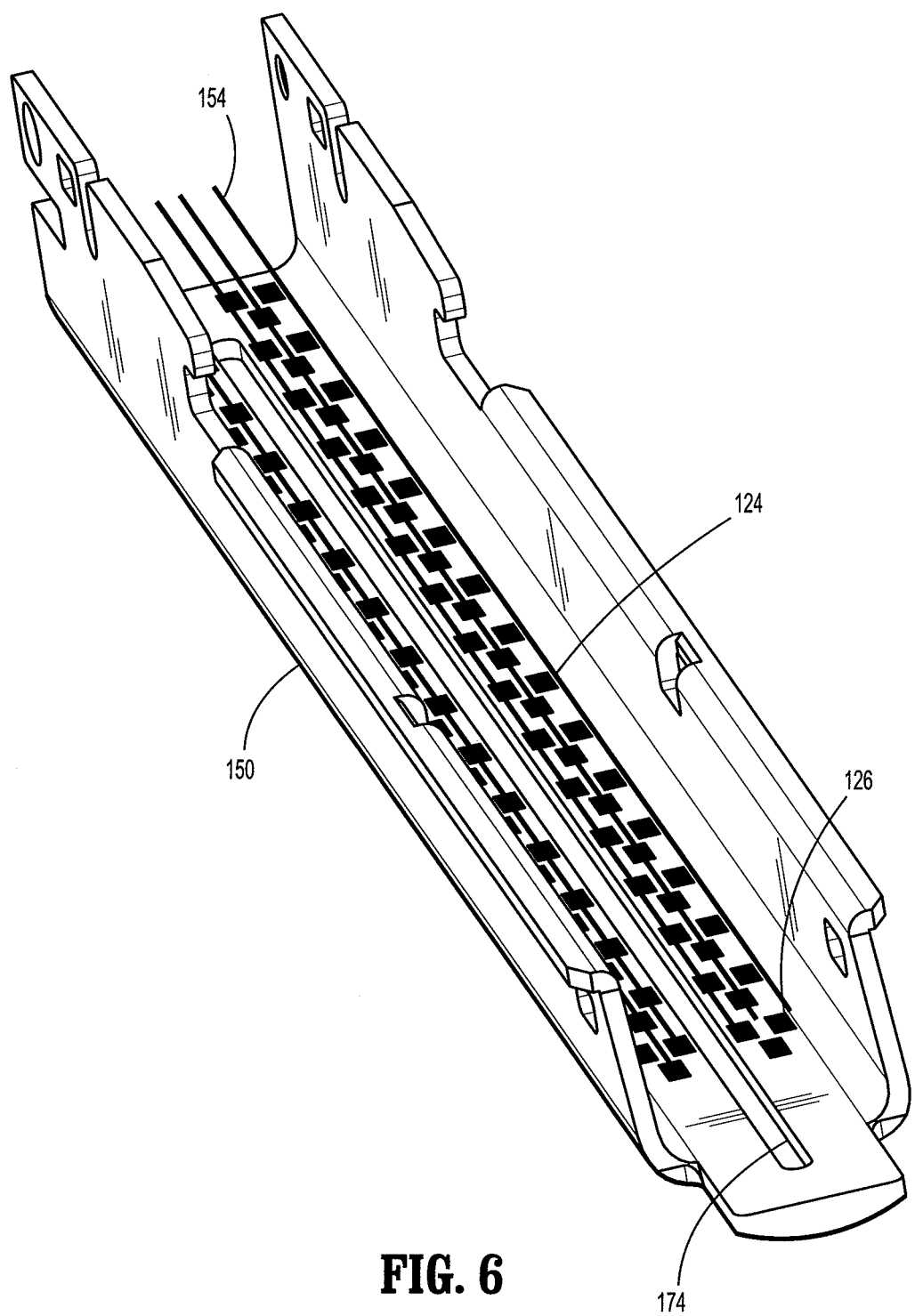
FIG. 6 is a perspective view of the interior channel of the cartridge with a printed pressure circuit disposed therein.

Referring now to FIG. 6, pressure responsive element 150 of one manifestation includes a circuit 124 wherein at least one lead 154 connects at least one pressure sensor 126. It is also contemplated that a plurality of pressure sensors 126 are disposed on surgical stapling apparatus 100, 200. In one instance, a lead 154 extends across a plurality of pressure sensors 126 in linear progression along the longitudinal axis, wherein at least one pressure sensor 126 corresponds to each fastener 114 or pusher member 130. Each linear row of fasteners 114 and/or pusher members 130 is connected by at least one lead 154 extending along the linear row and along the longitudinal axis of circuit 124. Circuit 124 is a flexible or a printed pressure circuit 124.

In this embodiment, circuit 124 is adhered to the top (working) surface of cartridge channel 128 so that circuit 124 can interact with actuation sled 132 that translates therethrough. In other words, circuit 124 is disposed within cartridge channel 128 to matingly engage actuation sled 132 as actuation sled 132 translates through cartridge channel 128 (FIGS. 3A-3B).

Figure 7:
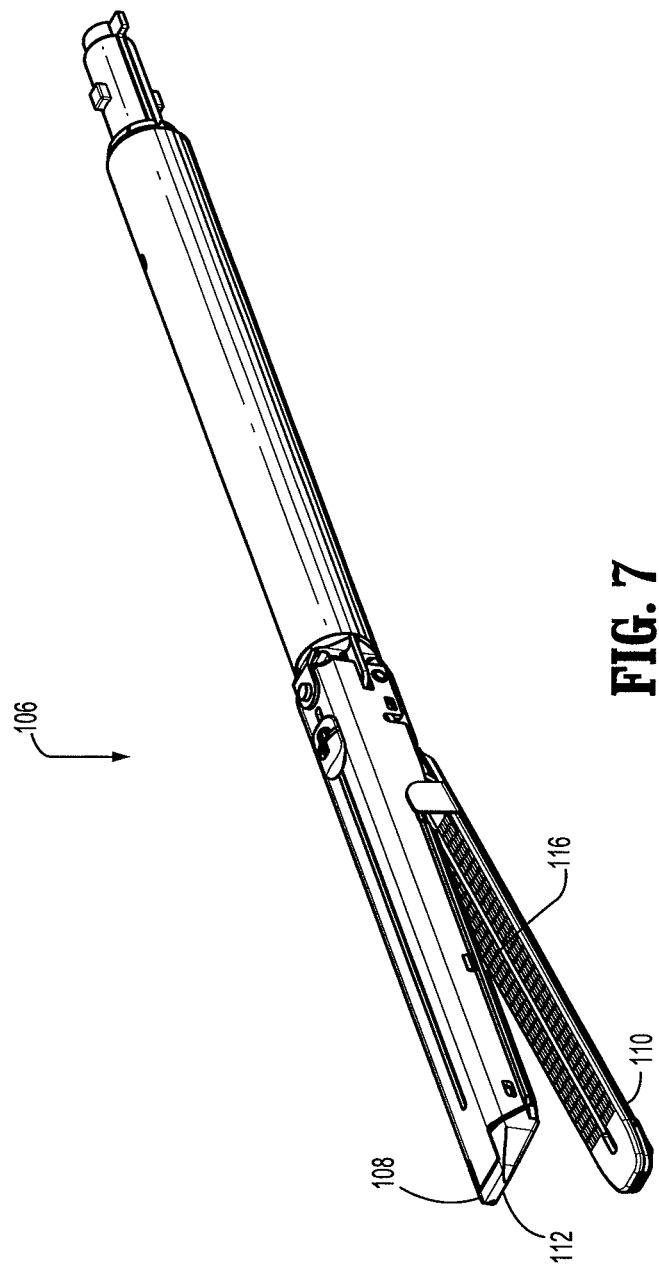
FIG. 7 is a perspective view of a removable end effector of FIGS. 1A and 1B illustrating a knife slot in one of the jaws.
Figure 8A:
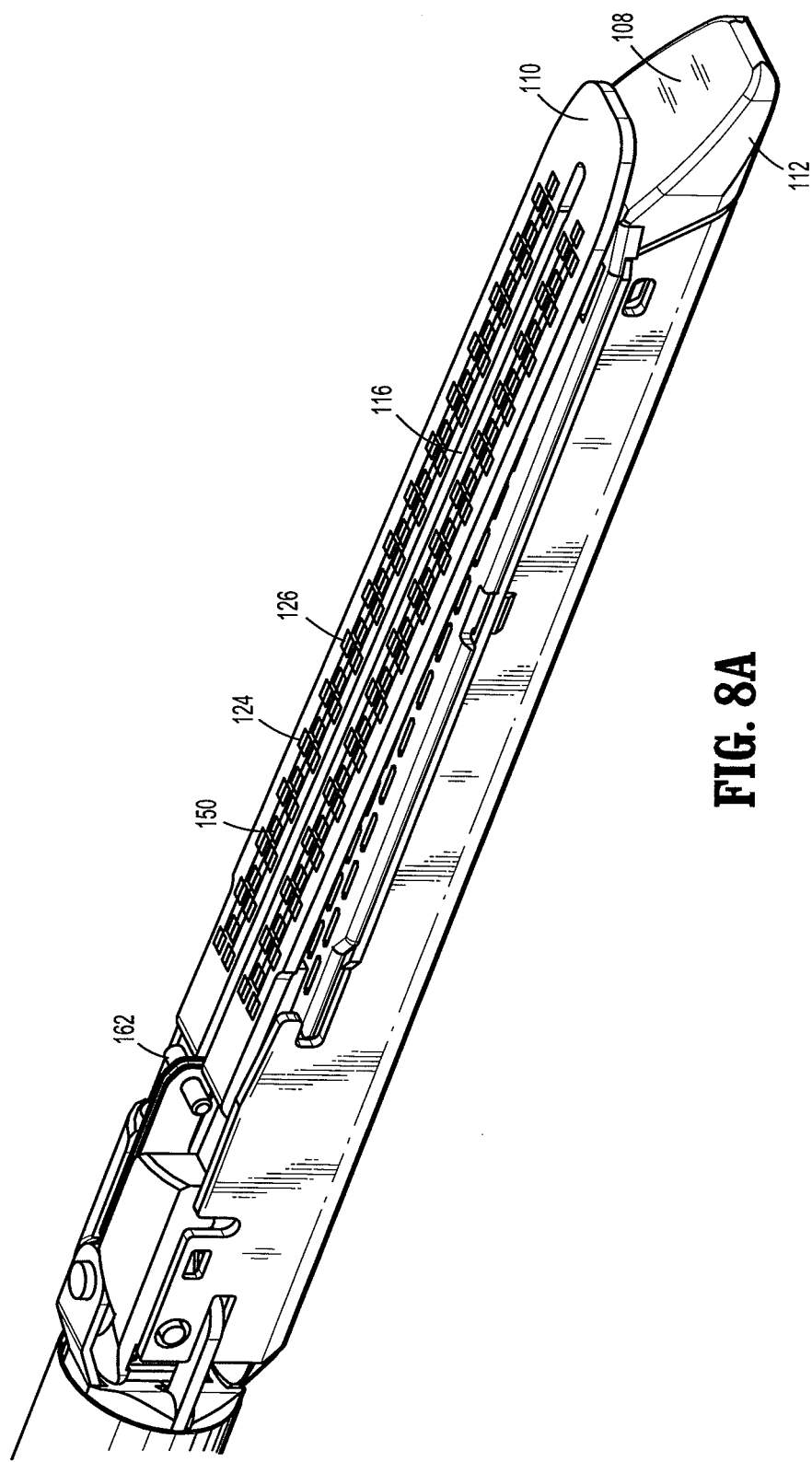
FIG. 8A is a perspective view of the end effector of FIG. 7 with the anvil cover removed for clarity showing a pressure circuit.
Figure 8B:
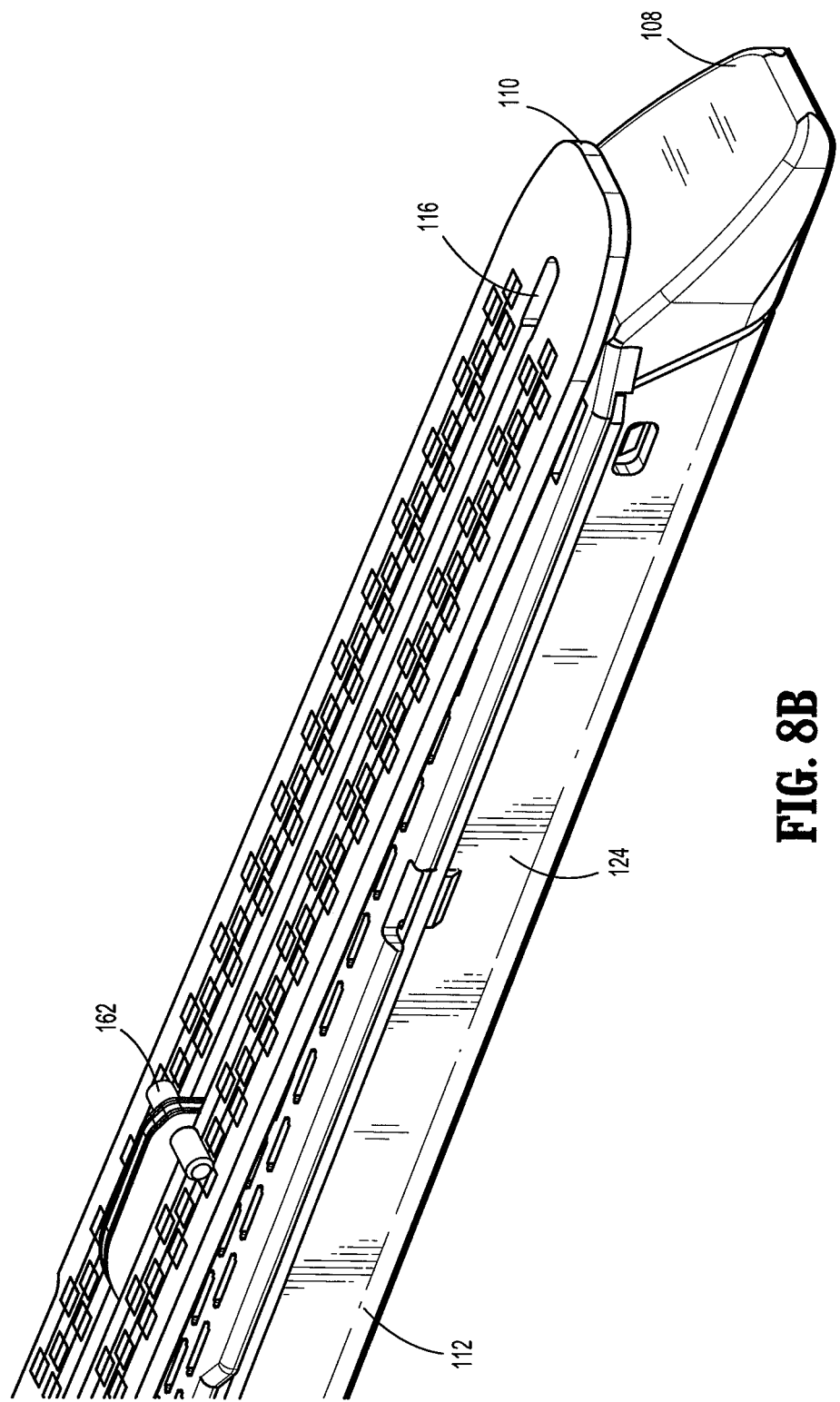
FIG. 8B is an enlarged perspective view of the embodiment disclosed in FIG. 8A.

FIGS. 7-8B show another embodiment of surgical stapling apparatus 100, 200. As seen in FIGS. 8A-8B, the surgical stapling apparatus 100, 200 includes a pressure responsive element 150 that includes a circuit 124 and is disposed on the external surface of at least one of the jaws 108, 110. Preferably, circuit 124 is disposed on the external surface of second jaw 110. This embodiment includes a beam 162. Beam 162 is disposed on the external surface of at least one of jaws 108, 110. Preferably, beam 162 is disposed on the external surface of second jaw 110. It is also contemplated that beam 162 is slidably seated in a groove 116 disposed within at least one of jaws 108, 110 and connected to actuation sled 132 (FIGS. 8A and 8B). Beam 162 is slidably seated in a groove 116 disposed within second jaw 110. Beam 162 is configured to translate along groove 116. The beam is an I-beam or an E-beam. Circuit 112 is envisioned to be very thin with respect to surgical stapling apparatus 100, 200, having dimensions at least geometrically thin enough as to not compromise or greatly impact the overall cartridge 112 size or function.

In some manifestations, pressure sensors 126 are staggered (FIGS. 3B, 6, 8A, 8B). Circuit 124 in one arrangement is staggered and optimized so that detailed information can be obtained for each fastener 114 or group of fasteners 114 formed by their associated pusher member 130. By having pressure sensors 126 staggered from the proximal to distal positions relative to fasteners 114 within surgical stapling apparatus 100, 200, surgical stapling apparatus 100, 200 can be configured to determine deployment timing and completion of each fastener 114. This is valuable for controlling surgical stapling apparatus 100, 200 with a controller 120 to verify limits with each specific cartridge 112 for clamping, distal stop, or home position. Controller 120 may have an analog or a microelectronic circuit.

As fastener 114 progression unfolds, pressure responsive element 150 communicates a pressure signal 152 to controller 120 through at least one communication means selected from the group comprising voltage, resistance, impedance, electromagnetism, radio frequency, current, inductance, capacitance, infrared, and optics. In operation, pressure responsive element 150 tracks the applied pressure as fasteners 114 are deployed and formed in progression (FIG. 5). In some cases, the applied pressure can be tracked in the form of waveform pulsations. When controller 120 recognizes irregular pressure patterns represented by pressure signal 152 communicated from pressure responsive element 150, controller 120 correspondingly registers an error and may be configured to emit an error code, emit a warning, stop fastener 114 formations, or even stop fastener 114 deployments.

Pressure responsive element 150 may also be configured for both linear and non-linear cartridge 112 configurations. It is envisioned that at least one of jaws 108, 110 includes a non-linear cartridge. In other words, pressure responsive element 150 can be used for linear cartridge surgical stapling apparatuses 100, 200 or non-linear cartridge surgical stapling apparatuses 100, 200 including curved, circular, or any other geometrically-shaped cartridge required to assess fastener quality or progression status.

Figure 11:
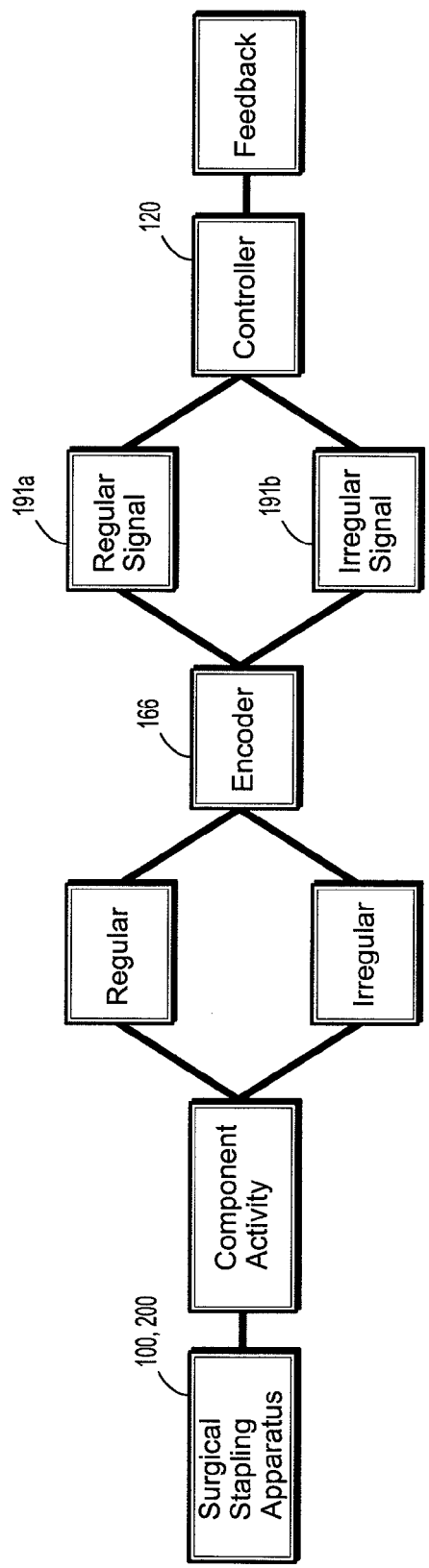
FIG. 11 is a block diagram of the encoder feature according to one embodiment of the present disclosure.

Often, surgical stapling apparatus 100, 200 can include a knife 164. In one manifestation of the present disclosure, surgical stapling apparatus 100, 200 is configured and dimensioned such that controller 120 prevents knife 164 from cutting. In other words, controller 120 includes an encoder 166, e.g., a knife cutting prevention feature. As seen in FIG. 11, one configuration contemplates the encoder 166 configured to recognize irregular behaviour of surgical stapling apparatus 100, 200. In some instances, encoder 166 is configured and dimensioned to recognize component positions relative to the pressure applied. The components of which are selected from the group comprising actuation mechanism 138, knife 164, actuator 136, actuation sled 132, pusher member 130, first jaw 108, and second jaw 110, or any combination thereof. Encoder 166 can be rotational, or even linear.

Figure 9:
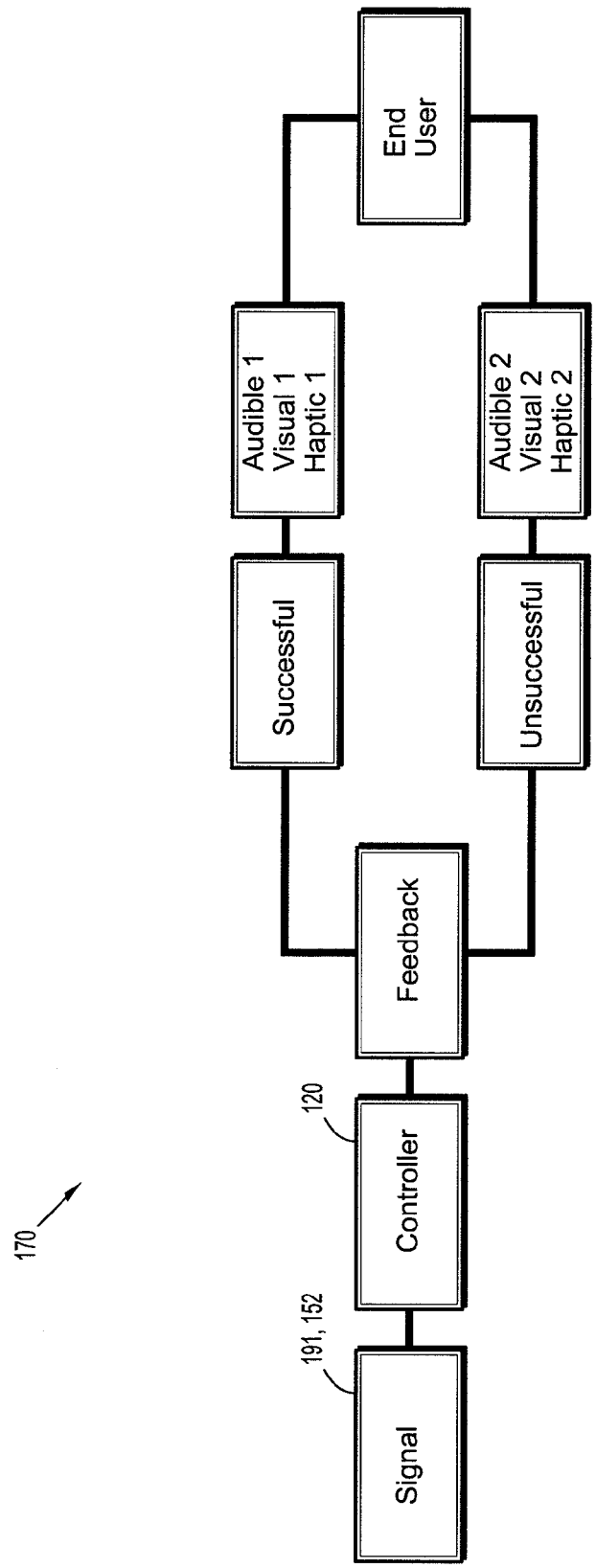
FIG. 9 is a block diagram of the end user feedback communication feature according to one embodiment of the present disclosure.

Referring to FIG. 9, controller 120, in some manifestations, includes an end user feedback communication feature 170. End user feedback communication feature 170 is configured to communicate feedback to an end user after receiving and deciphering a signal 152, 191 through at least one means selected from the group comprising audible (bells, speech, buzzers, beeps, etc.), visual (lights, LED's, LCD, or electroluminescent screens of varying colors, text, and/or symbols), and tactile (vibratory). For example, the feedback may be configured to indicate the successful or unsuccessful completion of a task such as initiation of fastener deployment progression, completion of fastener deployment and formation, individual fastener deployment, individual fastener formation, or other similar tasks recognized by a person of ordinary skill in the art.

To protect circuit 124 from tearing or abrasion and to attain accurate, repeatable feedback, a thin, hard surface material such as Kapton® polyimide film or a foil of titanium or steel alloy or a flash coated nickel, chrome or nitride coating can be laminated onto the top layer of circuit 124, defining a laminate 158. Furthermore, a lubricant coating 160 may also be applied to the laminate layer. Lubricant coating 160 is any low friction plastic, grease, PTFE blended material, or any other comparable lubricant. Lubricant 160 is beneficial for achieving a quality output pressure signal 152 and for improving the robustness of working components.

Figure 10:
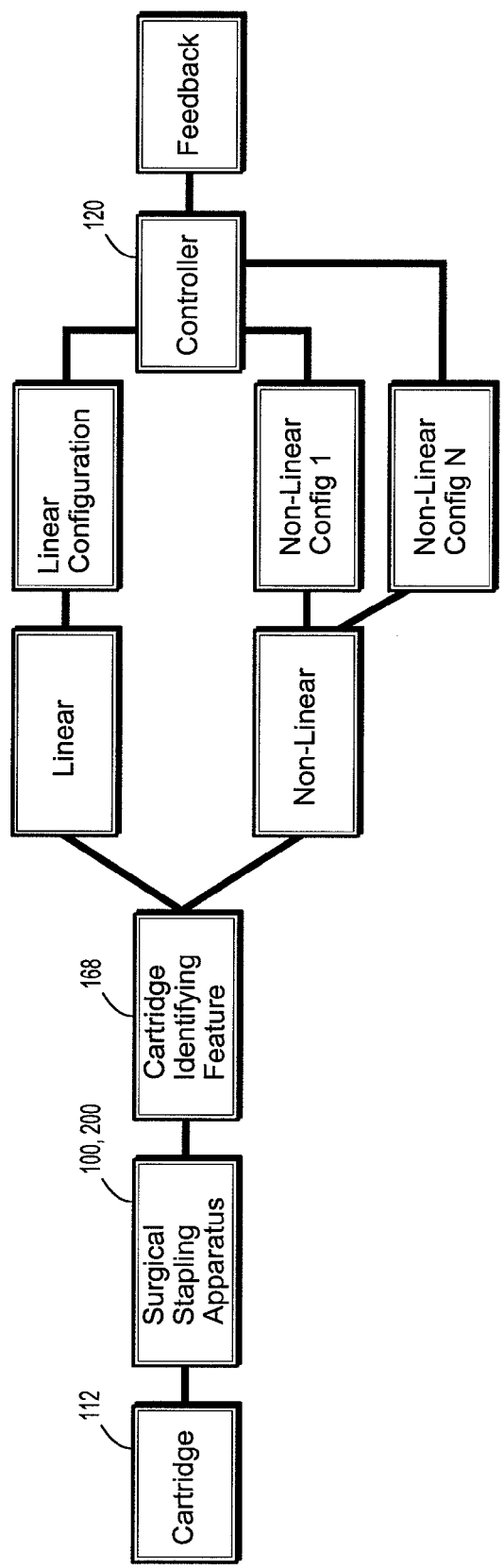
FIG. 10 is a block diagram of the cartridge identifying feature according to one embodiment of the present disclosure.

As seen in FIG. 10, surgical stapling apparatus 100, 200 may have a circuit 124 including a cartridge identifying feature 168. In particular, pressure responsive element 150 includes at least one circuit 124, wherein each circuit 124 has a specific electrical range or value of resistance, inductance, or impedance that can be read by controller 120 to determine the exact type of cartridge 112 or end effector 106 loaded for identification. With this feature, surgical stapling apparatus 100, 200 includes a controller 120 configured to set cartridge 112 or fastener 114 specific positional limitations and/or run mode.

Figure 4A:
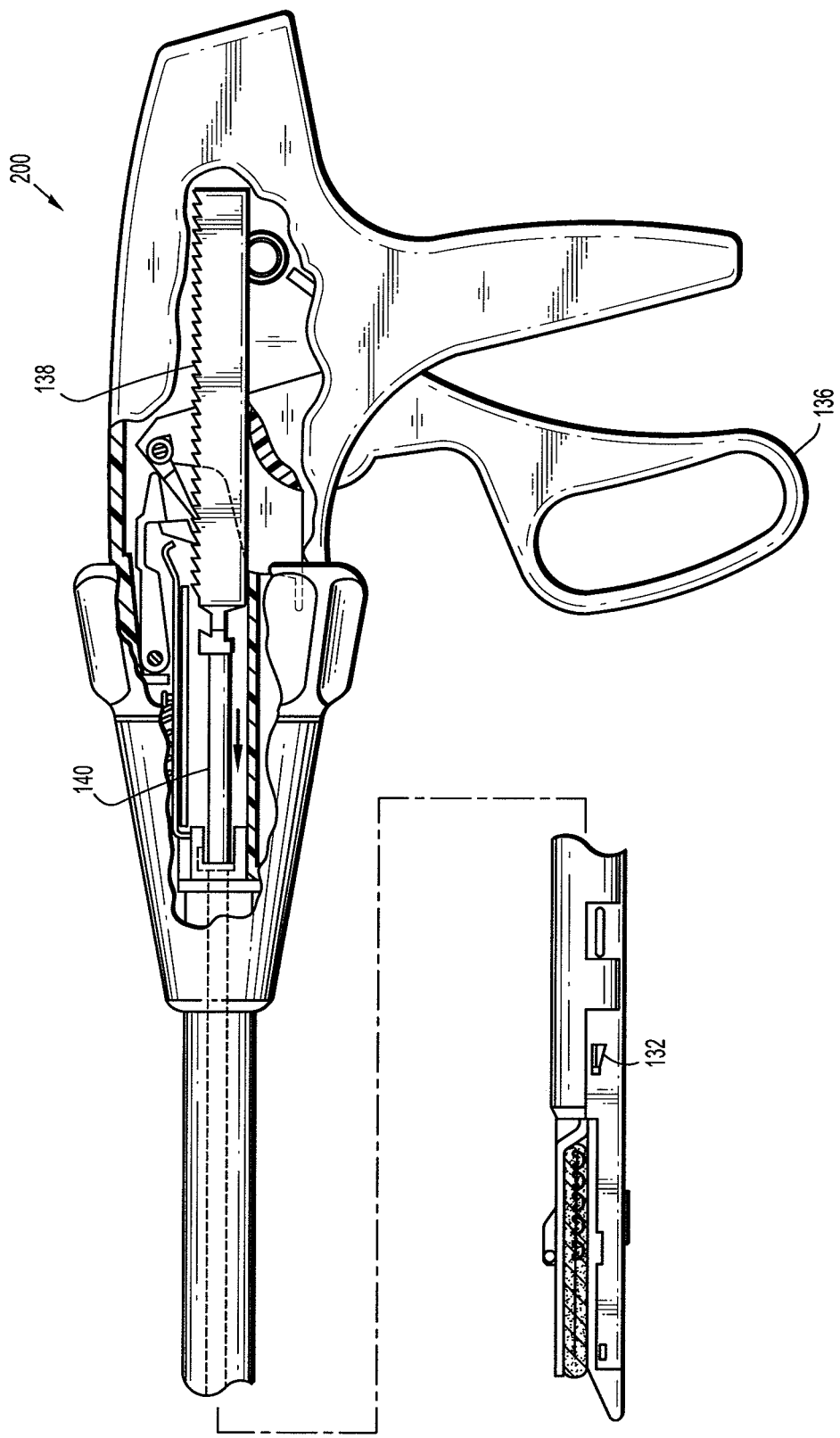
FIG. 4A is a side elevational view of the surgical stapling apparatus of FIG. 1B with the housing sectioned to illustrate the actuation mechanism when the actuator is manipulated through one an actuation stroke to apply a portion of the fasteners from the cartridge to tissue.
Figure 4B:
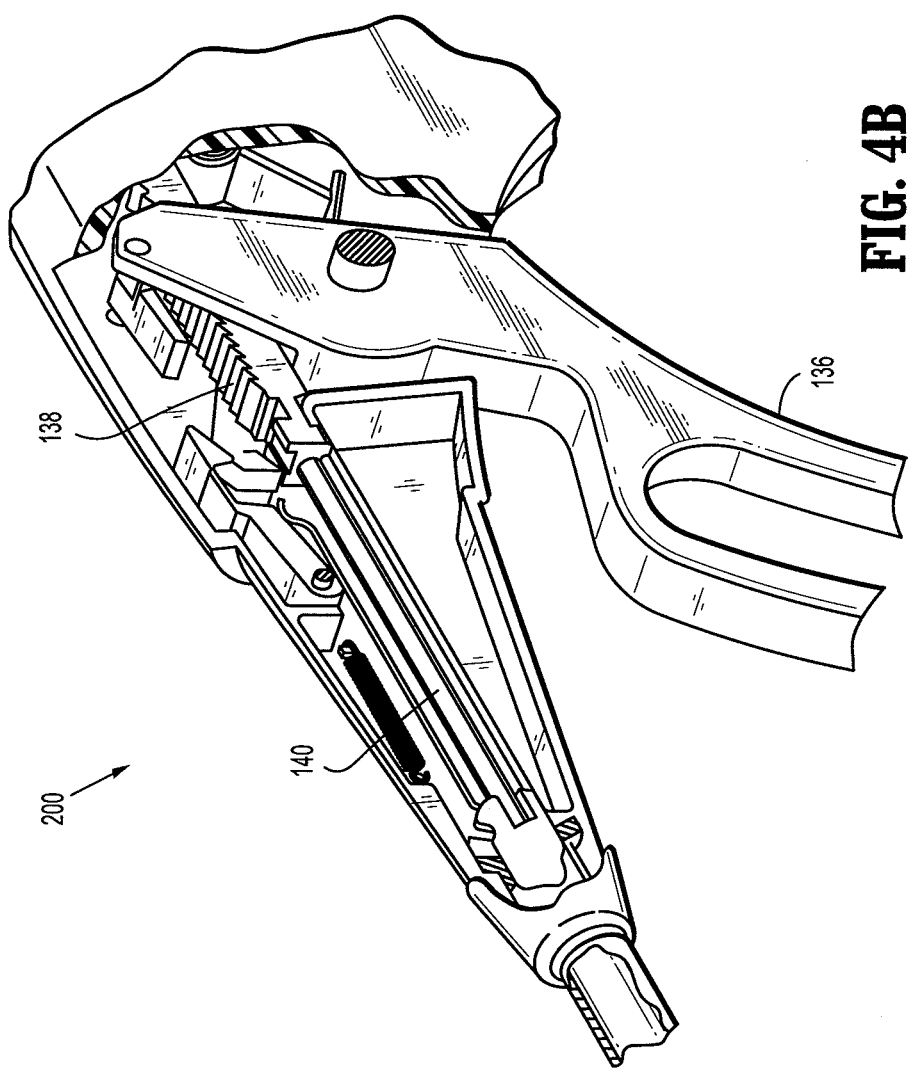
FIG. 4B is a perspective view in partial cross-section of the surgical stapling apparatus of FIG. 4A in accordance with the present disclosure.

In operation, when an end user (not shown) actuates actuator 136, actuating mechanism 138 causes actuation sled 132 to interact with pusher members 130 (FIG. 4A). In certain variations, actuator 136 includes separate actuating features for actuating actuation sled 132 and first and second jaws 108, 110. For example, an actuation sled actuator 136a is used to remotely actuate actuation sled 132, and a jaw actuator 136b is used to actuate first and second jaws 108, 110. Alternatively, a single actuator 136 is used to actuate both actuation sled 132 and jaws 108, 110. In another example, separate actuators 136 are connected to individual first and second jaws 108, 110.

Figure 1D:
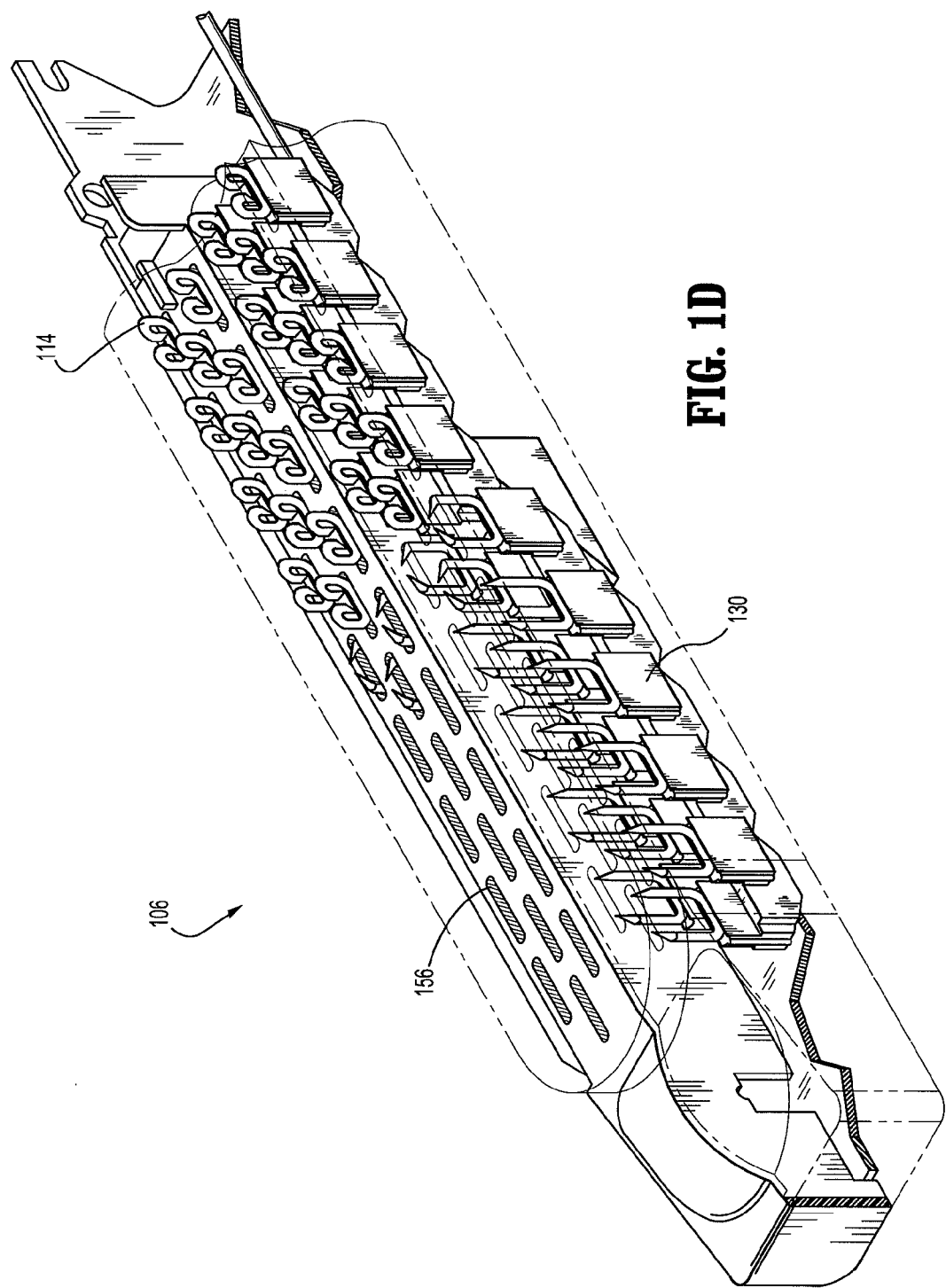
FIG. 1D is a perspective view of the end effector during a fastener applying operation as the wedge translates through the cartridge to sequentially eject the fasteners from the cartridge and drive them against one of the jaws to be formed thereby.

Upon actuation, actuation sled 132 wedges pusher members 130 upwards, forcing fasteners 114 up into opposing second jaw 110 surface, and in particular, into fastener-forming pockets 156 (FIG. 1D). From FIG. 1D, in its initial configuration fastener 114 is shaped in a substantially U-shaped configuration. In its fully formed configuration, fastener 114 is shaped in a substantially B-shaped configuration. In the process of transforming fastener 114 from the first configuration to the second configuration, second jaw 110 acts as an anvil and correspondingly compresses fastener 114 into its second configuration B-shape as fastener prongs 114a, 114b engage fastener-forming pockets 156. This resulting pressure applied to pressure responsive element 150 is therefore a result of the interaction between actuation sled 132 and pusher members 130.

In embodiments where pressure responsive element 150 includes a circuit 112 disposed within cartridge channel 128, the downward force of second jaw 110 onto the upwardly driving fastener 114, pusher member 130, and actuation sled 132 combination consequently causes reaction forces to pass through fasteners 114, pusher member 130, and actuation sled 132 combination in the opposing downward direction and onto circuit 112 and any pressure sensors 126, which correspondingly register the applied pressure. Pressure responsive element 150 then communicates a pressure signal 152 to controller 120, where pressure signal 152 is representative of the pressure applied to pressure responsive element 152. Controller 120 receives pressure signal 152 and selectively emits a response or feedback based on pressure signal 152.

In certain embodiments, pressure responsive element 150 includes a circuit 112 disposed on the external surface of one of jaws 108, 110. For example, when circuit 112 is disposed on the external surface of second jaw 110, applied pressure is displaced from beam 162, which is connected to actuation sled 132, onto circuit 112 as both beam 162 and actuation sled 132 translate longitudinally along first and second jaws 108, 110. In other words, as actuation sled 132 translates and engages pusher members 130, pusher members 130 drive fasteners 114 up into second jaw 110 and fastener-forming pockets 156. This consequently causes downward reaction forces to be displaced to beam 162 onto circuit 112 as actuation sled 132 pulls down beam 162 from the resultant downward reaction forces from fastener-forming pockets 156 pass through fasteners 114 and pusher members 130 onto actuation sled 132. Pressure sensors 126 correspondingly register the applied pressure. The pressure responsive element 150 than communicates a pressure signal 152 to controller 120, where pressure signal 152 is representative of the pressure applied to pressure responsive element 152. Controller 120 receives pressure signal 152 and selectively emits a response or feedback based on pressure signal 152.

In embodiments that include an encoder 166, encoder 166 is configured to recognize the irregular behaviour of a component of surgical stapling apparatus 100, 200 the components of which can be selected from the group comprising actuation mechanism 138, knife 164, actuator 136, actuation sled 132, pusher member 130, first jaw 108, and second jaw 110. In one example where encoder 166 is configured to monitor the positions of knife 164, and where encoder 166 recognizes an irregular position of knife 164, encoder 166 communicates the irregularity to controller 120 via an encoder signal 191 that may be either regular 191a or irregular 191b. Upon receiving an irregular signal 191b, controller 120 registers an error code, and in some instances, is configured to prevent cutting without fastening.

Encoder 166 communicates encoder signal 191 to controller 120 through at least one means selected from the group comprising voltage, resistance, impedance, electromagnetism, radio frequency, current, inductance, capacitance, infrared, and optics. It is also envisioned that controller 120 is configured and dimensioned to receive an encoder signal 191 from pressure responsive element 150 and to determine fastener 114 deployment and formation disparities with respect to the component behaviour, e.g., knife's 164 irregular positioning. Controller 120 is also configured and dimensioned to initiate an error code or modify fastener 114 deployment settings.

Turning now to FIGS. 12-16, a surgical device or end effector, for a powered surgical stapling apparatus according to another embodiment of the present disclosure, is shown and generally designated 500. End effector 500 includes a parallel separating jaw system wherein opposing jaws remain parallel relative to each other during approximation and separation. End effector 500 is configured to be capable of connection to powered, rotating drive shafts of an electromechanical power source (not shown). Thus, the end effector 500 can be a removable and replaceable component that can be connected to the shaft or elongate member of a surgical instrument. The shaft or elongate member can be flexible or rigid and itself can be interchangeable. A handle assembly can be manually actuated, motorized, or otherwise arranged to drive the operation of the end effector.

Figure 12:
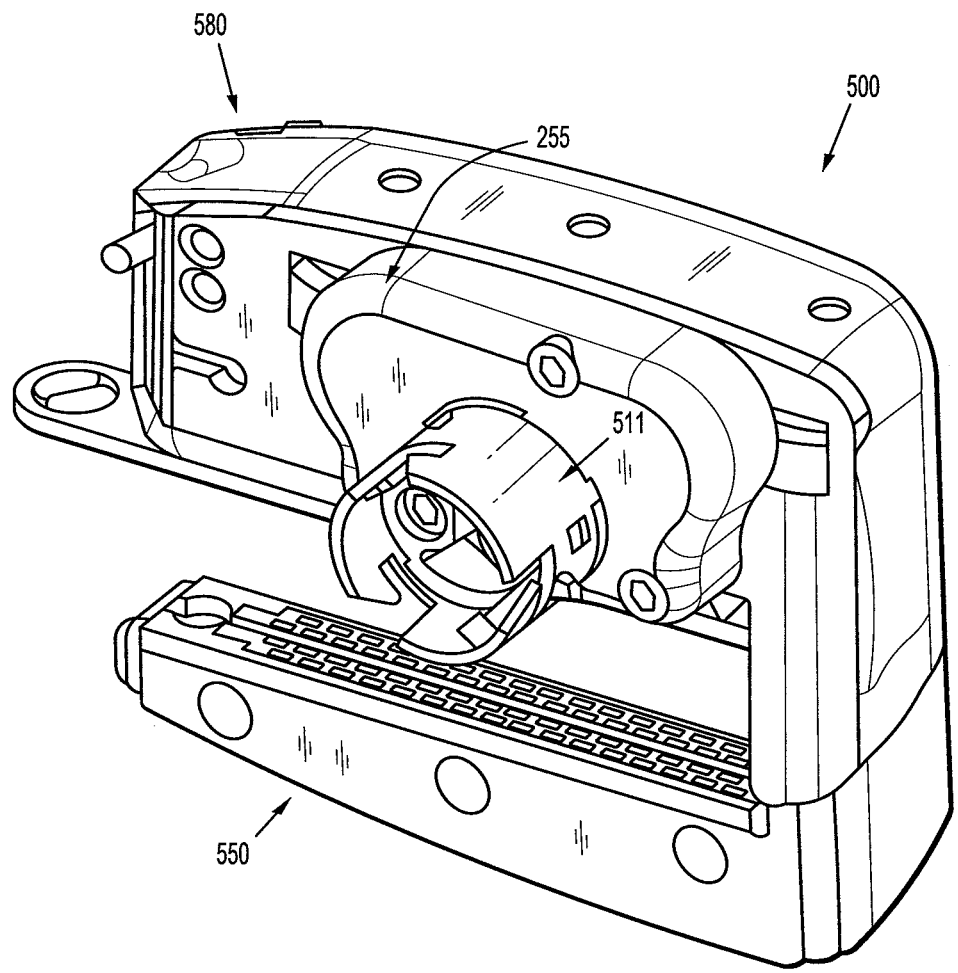
FIG. 12 is a perspective view of a surgical device or end effector for a powered surgical stapling apparatus according to another embodiment of the present disclosure.
Figure 13:
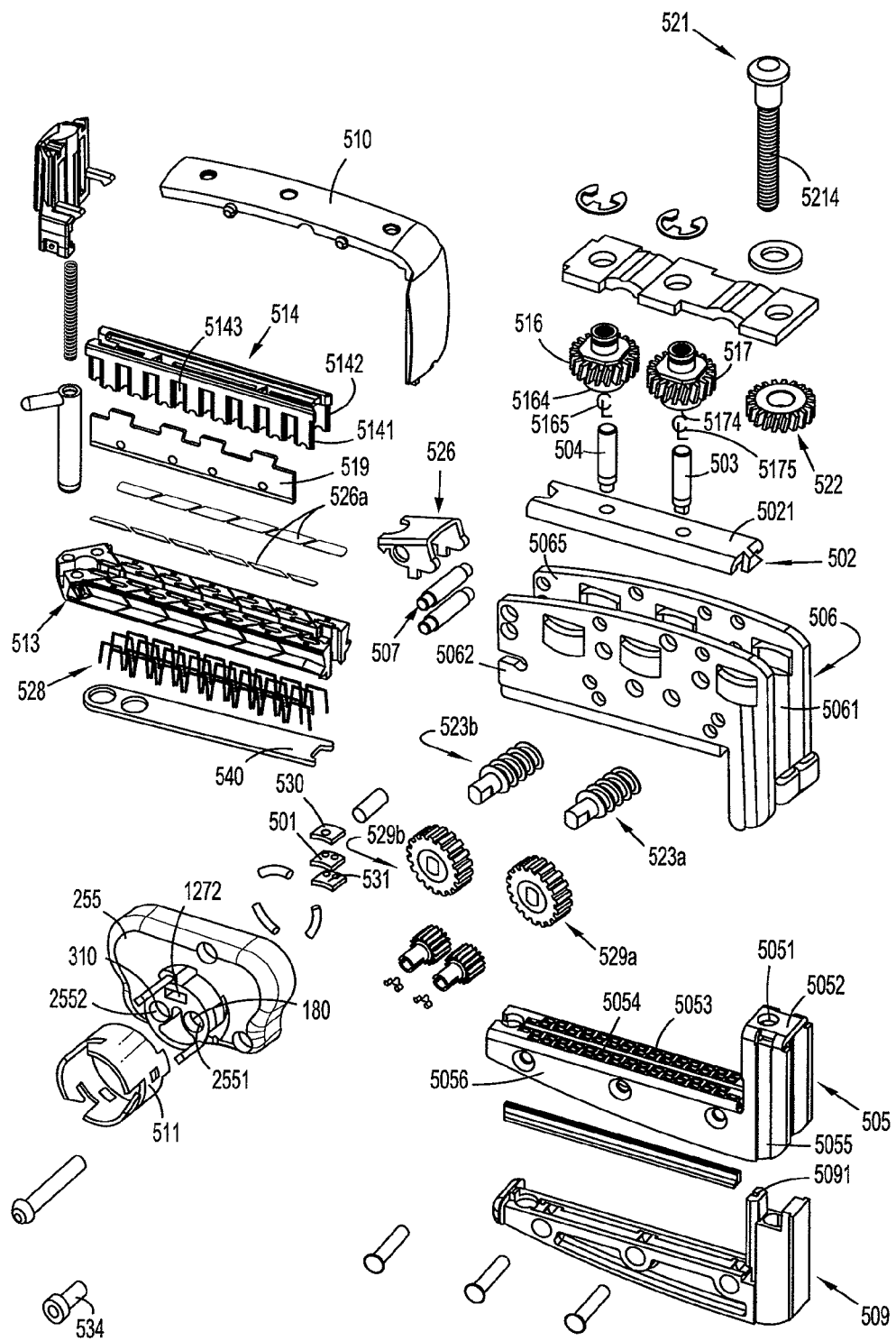
FIG. 13 is an exploded perspective view of the surgical device or end effector of FIG. 12.

As seen in FIGS. 12 and 13, end effector 500 includes a first jaw 580 and a second jaw 550, wherein first jaw 580 and second jaw 550 are in contact with each other at their respective first ends so as to enable parallel approximation and separation.

As seen in FIG. 13, second jaw 550 includes an anvil 505 having a vertically-disposed, internally-threaded bore 5051 at its upper end 5052, and a plurality of staple guides 5053 arranged in parallel rows along a region 5054 of anvil 505 that is opposite to, and corresponds to, first jaw 580.

With continued reference to FIG. 13, first jaw 580 includes a housing frame 506 defining a pair of internally disposed guides 5061 along which a pair of ribs 5055 of anvil 505 of second jaw 550 may travel, so that housing frame 506 may move toward and away from anvil 505 while remaining parallel with anvil 505.

A gear housing 255 is mounted to one side 5062 of housing frame 506. A quick-connect coupling 511 is mounted onto gear housing 255. A memory module 501 is arranged in gear housing 255 and includes a connector 2554 that extends through, or is accessible through, an opening 2553 of gear housing 255. Memory module 501 is maintained in position within gear housing 255 by an inboard shim 530 and an outboard shim 531. Gear housing 255 includes a first drive socket 180 and a second drive socket 310. In this embodiment, first drive socket 180 of gear housing 255 includes a first pinion 508a, and second drive socket 310 of gear housing 255 includes a second pinion 508b.

Each of first and second pinions 508a and 508b engage respective first and second spur gears 529a and 529b. First spur gear 529a non-rotatably engages a first worm 523a. Second spur gear 529b non-rotatably engages a second worm 523b. A threaded portion of each of first worm 523a and second worm 523b is disposed within frame housing 506.

Also disposed within frame housing 506 is a gear 522 which threadably engages threaded portion of first worm 523a. Gear 522 non-rotatably engages a screw 521. Screw 521 includes externally-disposed threads 5214, which engage internally-threaded bore 5051 of anvil 505.

A first gear 516 and a second gear 517 are disposed within frame housing 506. First gear 516 and second gear 517 are positioned on opposite sides of and engaged with second worm 523b. Specifically, first gear 516 engages a first side of second worm 523b, and second gear 517 engages a second side of second worm 523b.

An externally-threaded screw 504 is disposed through an internally-threaded bore 5164 of first gear 516, and an externally-threaded screw 503 is disposed through an internally-threaded bore 5174 of second gear 517. Since first and second gears 516 and 517 are located on, and engage, opposite sides of second worm 523b, internally-threaded bores 5164 and 5174 of first and second gears 516 and 517, as well as externally-threaded screws 504 and 503, may be oppositely threaded relative to each other. Both screws 503 and 504 are fixedly coupled to a top surface 5021 of a thrust plate 502 that is positioned between opposite side walls of housing frame 506.

A staple pusher 514, which may be one-piece, is attached to a bottom surface of thrust plate 502. Staple pusher 514 includes parallel rows 5141 and 5142 of downwardly-disposed teeth 5143, each of which corresponds to and aligns with a staple guide 5053 of anvil 505. A knife 519 having a cutting edge 5191 (shown facing downwardly in FIG. 13) is disposed between the parallel rows of downwardly-disposed teeth 5143 of staple pusher 514.

A staple holder or cartridge 513 is disposed below staple pusher 514. Staple cartridge 513 defines vertically-disposed slots 5132, each of which corresponds to and aligns with downwardly-disposed teeth 5143 of staple pusher 514 and with staple guides 5053 of anvil 505. A staple 528 is provided in each slot 5132. Staple cartridge 513 also includes a longitudinally-disposed slot 5131 through which knife 519 may be passed.

A staple retainer 540 is provided and is configured to cover the bottom surface of staple cartridge 513 so as to maintain staples 528 within staple cartridge 513 and to prevent foreign material from entering slots 5132 of staple cartridge 513 during shipping of end effector 500.

A housing top 510 is provided and is arranged between opposite sides 5062 and 5065 of housing frame 506 and protects the components within housing frame 506.

Reference may be made to U.S. patent application Ser. No. 10/094,051 (U.S. Patent Publication No. 2003/0130677), filed on Mar. 8, 2002, entitled "Surgical Device", the entire contents of which are incorporated herein by reference, for a more detailed discussion of the components, construction and operation of end effector 500. In addition, the end effector is connectible to a powered instrument handle which may include an elongate shaft. A separate, detachable shaft may also be used. As disclosed in Pub. No. 2003/0130677, the shaft may be a flexible shaft extending from a housing and detachably attached thereto via a first coupling. The distal end of flexible shaft may include a second coupling adapted to detachably attach the end effector described above, to the distal end of the flexible shaft. The second coupling may also be adapted to detachably attach a different type of end effector. In another example embodiment, the distal end of the flexible shaft may be permanently attached to or be integral with a surgical instrument handle.

The shaft may include a first rotatable drive shaft and a second rotatable drive shaft, such as, for example, braided or helical drive cables. The drive shafts may be configured to transmit low torque but high speed, the high-speed/low-torque being converted to low-speed/high-torque by gearing arrangements disposed, for example, at the distal end and/or the proximal end of the drive flexible shaft, in the surgical instrument or attachment. Electro-mechanical driver elements disposed in a remote power console, or in a powered instrument handle, are used to operate the rotatable shafts.

In certain preferred embodiments, a controller is provided in the housing of a remote power console, or in the powered instrument handle, and is configured to monitor and/or control some or all functions and operations of the end effector attached to the flexible shaft, as well as the instrument as whole. A memory unit is provided and may include memory devices, such as, a ROM component, a RAM component, etc. The RAM and ROM components are in electrical and logical communication with controller via appropriate wiring. Memory units may also communicate with the controller, or other components, wirelessly.

Turning now to FIGS. 13-16, a more detailed discussion of end effector 500, including staple cartridge 513 according to the present disclosure, is provided. As seen in FIGS. 13-16, staple cartridge 513 is segmented along an axial length thereof. In particular, staple cartridge 513 is formed from a plurality of individual, separately movable body members or segments 513a extending axially along a length of staple cartridge 513. Collectively, segments 513a form a staple guide 5130. Each segment 513a is free to move in a direction transverse or orthogonal to a plane defined by the tissue contacting surface of staple cartridge 513.

As seen in FIGS. 14A-16, slots 5132, for retaining staples 528 therein, are arranged in at least two, longitudinally extending, parallel rows disposed on each side of knife slot 5131 (for passage of knife 99). Slots 5132 of each pair of rows are off-set or staggered with respect to one another, wherein slots 5132 of one row are disposed between slots 5132 of an adjacent row.

Figure 14A:
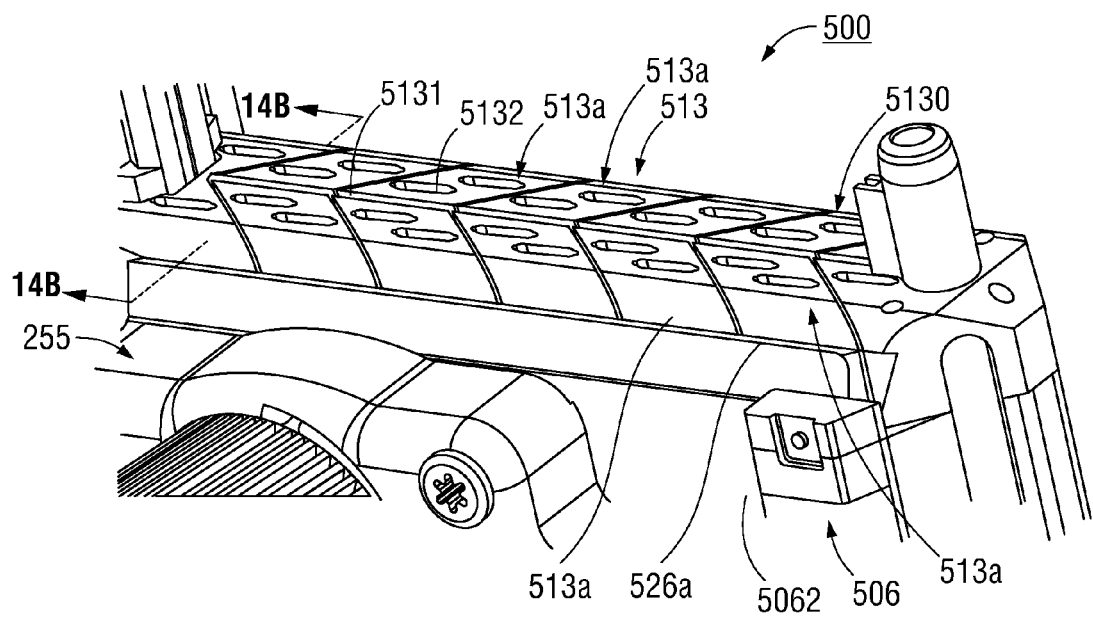
FIG. 14A is an enlarged perspective view illustrating a staple guide supported in a staple cartridge frame housing of the surgical device or end effector of FIG. 12.
Figure 14B:
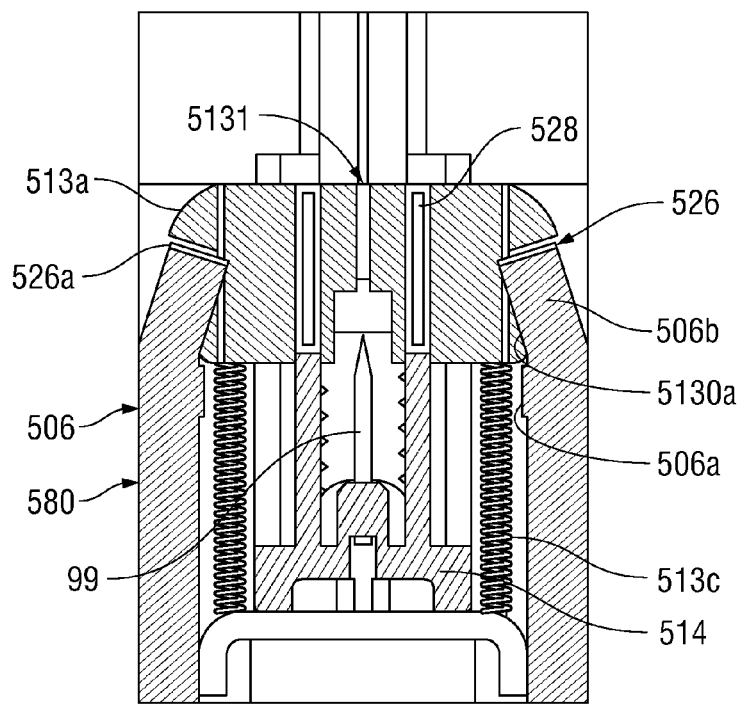
FIG. 14B is an enlarged cross-sectional view of the end effector of FIG. 12, as taken through 14B-14B of FIG. 14A.
Figure 15:
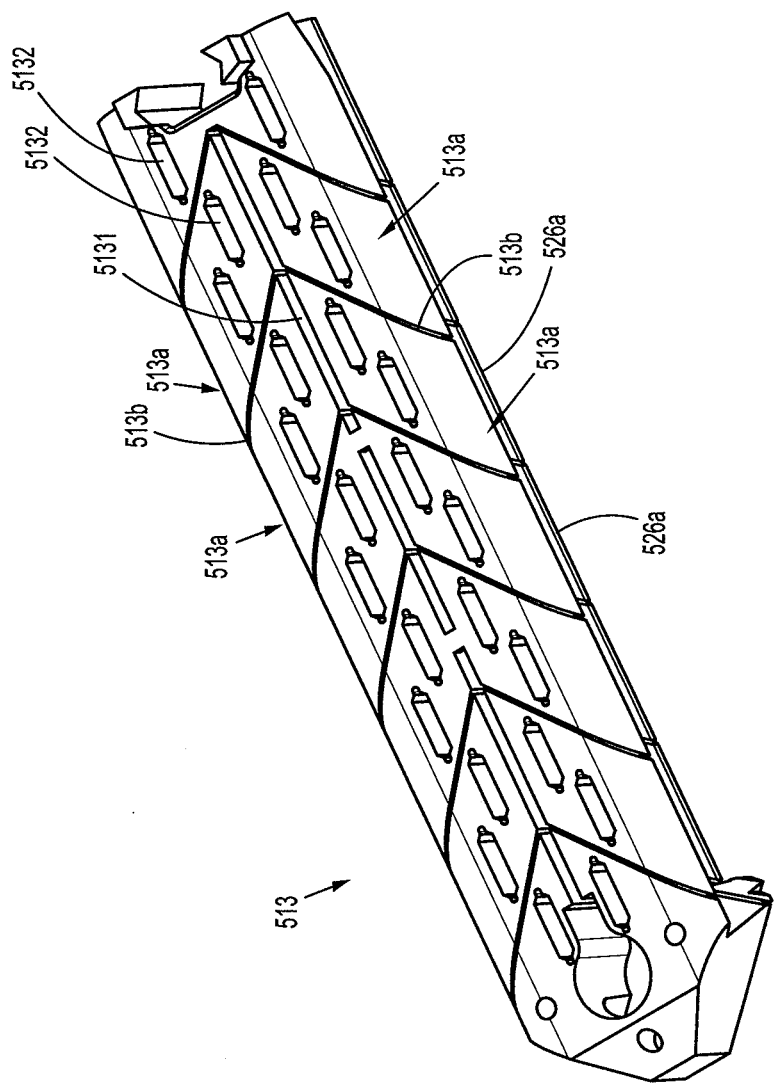
FIG. 15 is an enlarged perspective view of the staple guide of the surgical device or end effector of FIG. 12.
Figure 16:
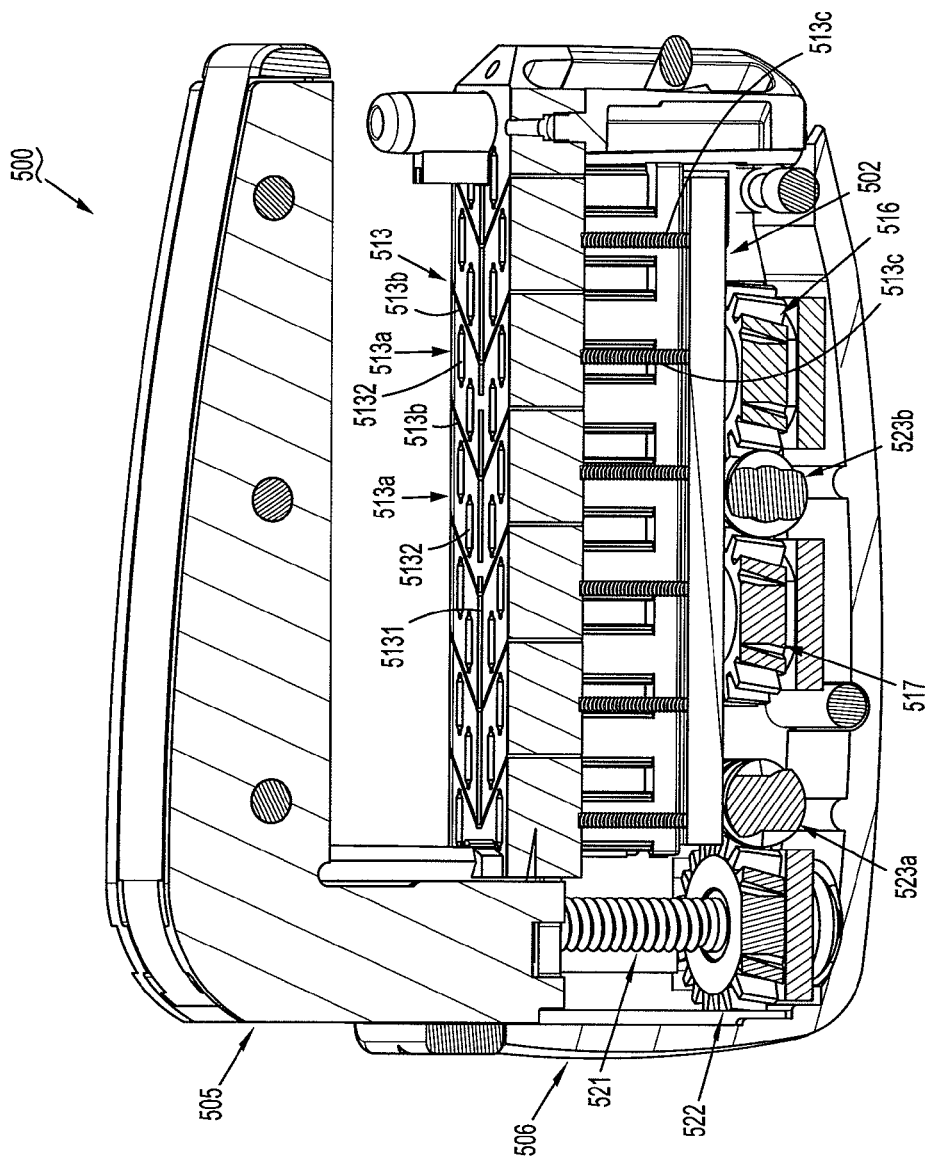
FIG. 16 is a cross-sectional view of the surgical device or end effector of FIG. 12, as taken through 16-16 of FIG. 12.

As best shown in FIGS. 14A-14B, housing frame 506 of first jaw 580 includes one or more locking features 506a, projecting from an inner surface of housing 506, configured to limit movement of one or more of segments 513a of staple guide 5130. In particular, when segments 513a of staple guide 5130 are forced downward by tissue, locking features 506a interfere with segments 513a to prevent further downward movement thereof. Thus, when in a fully clamped configuration, segments 513a are locked in place which is facilitated by virtue of locking features 506a. Notably, the locking of segments 513a in place at varying heights due to various applied pressures, resulting from various tissue thicknesses, will not affect staple formation because staple pusher 514, which may be a one-piece as discussed above, or other staple pusher or pushers, maintains the same stroke independent of staple guide 5130 or the position of any of its segments 513a.

As best illustrated in FIG. 14B, housing frame 506 of first jaw 580 includes first angled portions 506b that are disposed in registration with and in contact with second angled portions 5130a of segments 513a to maintain segments 513a in a substantially fixed position (i.e., excluding the tissue responsive movement discussed herein) relative to housing frame 506 of first jaw 580. The locking features may include detents, frictional members, pawls, levers and the like. Any of the embodiments disclosed herein can include the locking features and movable segments of the staple guide.

Each segment 513a of staple cartridge 513 is axially separated from one another by a transverse dividing line 513b that extends transversely across staple cartridge 513 and that does not extend across any staple slot 5132. In other words, the transverse dividing line 513b extends between axially adjacent slots 5132. Additionally, each segment 513a is sized so as to include a single slot 5132 from each of the adjacent rows of slots. However, it is contemplated that more than one slot 5132 from each row of slots may be disposed within each segment 513a.

With continued reference to FIGS. 14A-16, end effector 500 further includes a pressure sensing film 526 interposed between staple cartridge 513 and sides 5062, 5065 of housing frame 506. In particular, pressure sensing film 526 includes a plurality of individual pressure sensing film segments 526a interposed, one each, between respective segments 513a of staple cartridge 513 and sides 5062, 5065 of the housing frame 506.

As seen in FIG. 13, each segment 513a of staple cartridge 513 is floating above respective pressure sensing film segments 526a by respective biasing members 513c, in the form of compression springs. In particular, biasing members 513c are interposed between respective segments 513a of staple cartridge 513 and thrust plate 502 (see FIGS. 13 and 16) of end effector 500. In this manner, in use, the gap or distance from the tissue contacting surface of staple cartridge 513 to the tissue contacting surface of anvil 505 may adjust or vary depending on the thickness of tissue clamped between first jaw 580 and second jaw 550.

In accordance with the present disclosure, staple cartridge 513 of end effector 500, when coupled to an intelligent surgical device, instrument or apparatus 100, as described above, or when coupled to the electro-mechanical driver system, as shown and described in U.S. patent application Ser. No. 10/094,051 (U.S. Patent Publication No. 2003/0130677), filed on Mar. 8, 2002, entitled "Surgical Device", the entire content of which is incorporated herein by reference, is capable of adjusting to accommodate different thicknesses present in a section of tissue that is clamped between first jaw 580 and second jaw 550.

Each pressure sensing film segment 526a is capable of sensing a force that is exerted on each segment 513a of staple cartridge 513 during a clamping or approximation of first jaw 580 and second jaw 550 and/or during a firing of end effector 500. Each segment 513a of staple cartridge 513 is spring loaded to a pre-set height, by biasing members 513c, during an unloaded or unclamped condition.

Each pressure sensing film segment 526a may be in electrical communication with the controller 120 (see FIG. 2). In this manner, signals sensed by pressure sensing film segments 526a may be transmitted to controller 120 for processing and/or analysis, and the processed and/or analyzed.

In operation, upon clamping or approximation (i.e., clamp up) of first jaw 580 and second jaw 550, each segment 513a of staple cartridge 513 becomes individually compressed (i.e., pressed against a respective pressure sensing film segment 526a) by the tissue by an amount dependent upon the force exerted on each section 513a of staple cartridge 513. Due to the floating nature of each segment 513a of staple cartridge 513, each segment 513a is capable of slight movement in a side-to-side or lateral direction and/or in a longitudinal direction.

The pressure sensing film segments, in certain embodiments, are connected to the controller and data are stored in the memory units and/or transmitted to other components. The memory units of the controller (which may be a remote unit, or may be incorporated in a powered instrument handle attached to the shaft and end effector) include data concerning desired parameters or ranges for the operation of the end effector and instrument as a whole. For example, the forces exerted on each segment 513a of staple cartridge 513 is determined by pressure sensing film segments 526a in a manner substantially similar to pressure responsive element 150, as described above. The forces determined, detected of measured by pressure sensing film segments 526a may be displayed on a monitor, a display provided on the surgical device, or the like (not shown). It is contemplated that the monitor will display the forces exerted on each individual segment 513a of staple cartridge 513 as well as the overall force exerted on the entire length of staple cartridge 513.

The forces measured by the pressure sensing film segments can be monitored over time. In other words, how the forces vary as the staples are ejected and formed against the anvil can be monitored, transmitted to the controller, transmitted to other components, stored in the memory units of the controller, compared to data concerning desired profiles for staple forming and/or used to provide information to the surgeon or used to affect the operation of the instrument.

Pressure sensors that can be used include but are not limited to electrical circuits that measure or monitor differences in one or more of resistance, conductance, impedance and capacitance. The sensor may incorporate one or more laminated layers of resistive and conductive substrates. Other sensors are contemplated.

In accordance with the present disclosure, the intelligent surgical device, instrument or apparatus 100, as described above, or the electro-mechanical driver system, as shown and described in U.S. patent application Ser. No. 10/094,051 (U.S. Patent Publication No. 2003/0130677), will be able to interpret a magnitude of the forces and determine whether conditions are acceptable to continue clamping/approximating first jaw 580 and second jaw 550 or if conditions are acceptable for firing of end effector 500.

Additionally, in accordance with the present disclosure, the intelligent surgical device, instrument or apparatus 100, as described above, or the electro-mechanical driver system, as shown and described in U.S. patent application Ser. No. 10/094,051 (U.S. Patent Publication No. 2003/0130677), will be able to determine if obstructions are present in the tissue that is clamped between first jaw 580 and second jaw 550 and whether conditions are acceptable for firing of end effector 500 based on the loads and/or forces exerted on staple cartridge 513.

Accordingly, in view of the floating or spring biased nature of staple cartridge 513, and segments 513a thereof, an adjustment or accommodation of staple cartridge 513 is more forgiving in tissues with inconsistent thicknesses, with obstructions and/or which are diseased. Additionally, the force sensing capability of staple cartridge 513 can provide the surgeon with an indication of the amount of compressive force each portion or segment of the tissue is under during a clamping/approximating of the first jaw 580 and second jaw 550 and/or during a firing of end effector 500. Also, since staple cartridge 513 is segmented and there are a plurality of pressure sensing film segments 526a disposed along an entire length of staple cartridge 513, the surgeon can be provided with information regarding the presence of an obstruction in the tissue clamped between first jaw 580 and second jaw 550 and an indication of the location of the obstruction along the length of staple cartridge 513.

By providing the surgeon with an indication of the location of the obstruction along the length of staple cartridge 513, the surgeon may move end effector 500 to another location or section of tissue, if necessary, in order to avoid hitting the obstruction during the stapling or firing procedure.

In operation, if the forces exerted on a particular segment 513a of staple cartridge 513 exceed a predetermined threshold value and/or if an average force exerted on staple cartridge 513 exceeds a predetermined threshold value, then the controller may register an error and may be configured to emit an error code, emit a warning and/or stop the firing procedure.

Figure 17:
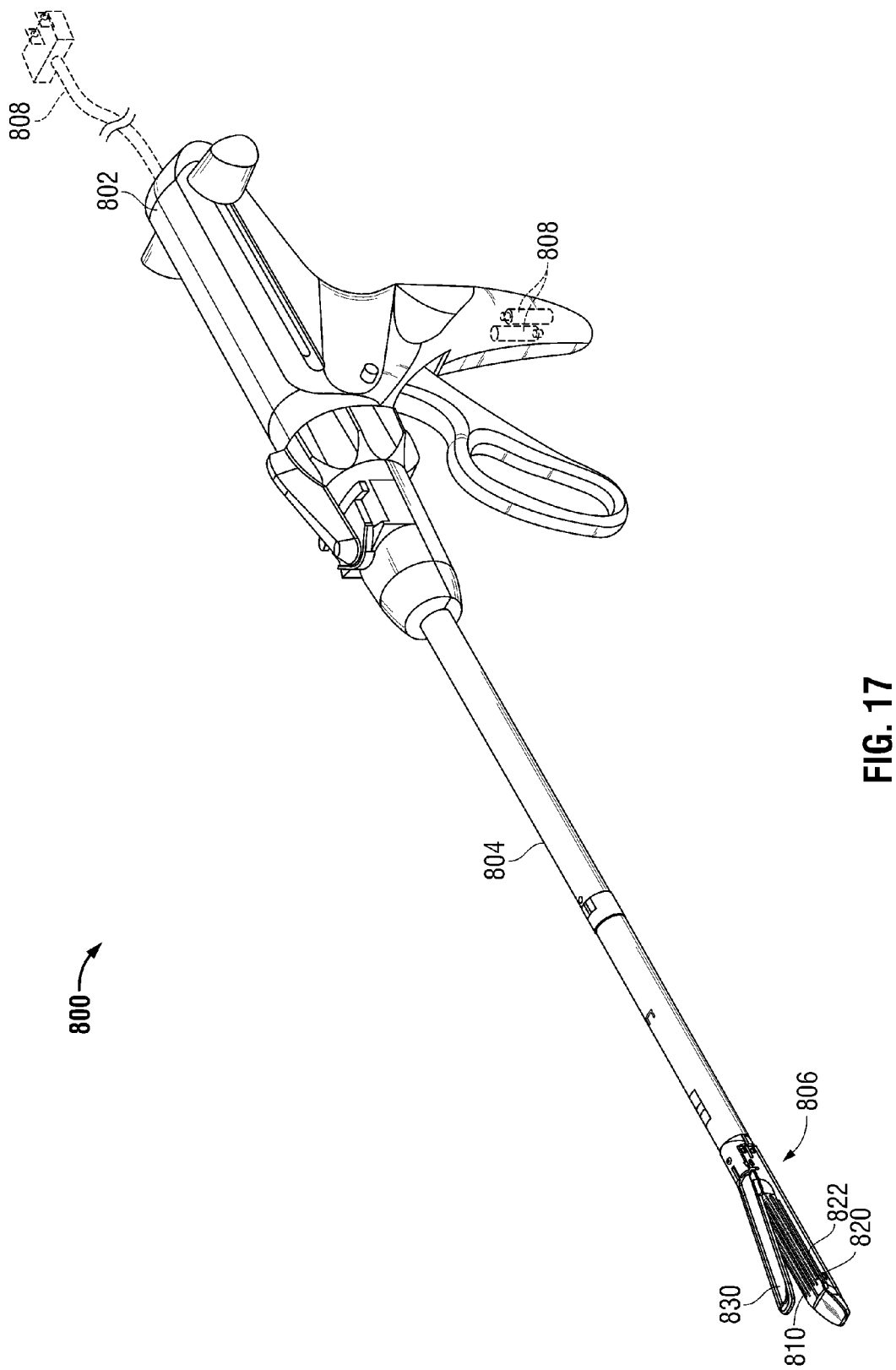
FIG. 17 is a perspective view of another embodiment of a surgical stapling apparatus in accordance with the present disclosure.
Figure 18B:
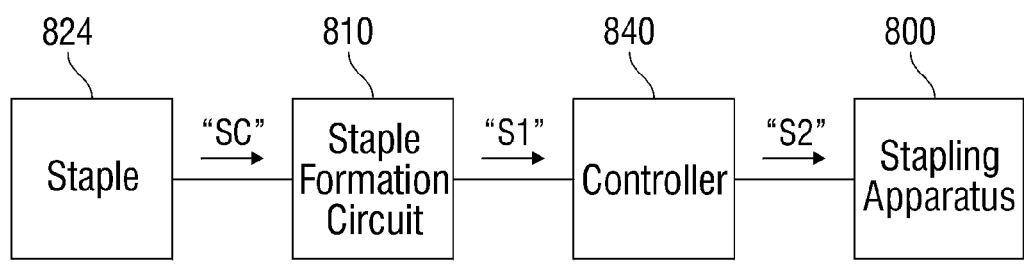
FIG. 18B is a block diagram illustrating the operation of the surgical stapling apparatus of FIG. 17.

Turning now to FIG. 17, one embodiment of a surgical stapling apparatus 800 is similar to surgical stapling apparatus 100 and is described herein only to the extent necessary to describe the differences in construction and operation. Surgical stapling apparatus 800 includes a housing or handle 802, an elongated member 804, an end effector 806, an energy source 808, and a staple formation circuit 810 (FIG. 18A). Energy source 808 is in electrical communication with staple formation circuit 810 and provides one or both of a voltage potential and a voltage waveform. In particular, energy source 808 may be a battery (e.g., a smart battery) for providing voltage potential and/or an electrosurgical energy source (e.g., a generator) for providing a voltage waveform. The voltage potential and/or the voltage waveform may be in a microelectronic voltage and current range. The voltage wave or voltage potential is monitored by a controller 840 (e.g., a microelectronic control circuit, FIGS. 18B and 22) which reads the resistance, and/or impedance, and/or inductance, and/or capacitance of a parallel or series circuit configuration discussed in greater detail below.

Elongated member 804 extends from housing 802. End effector 806 is disposed on an end of elongated member 804 and has a first jaw 820 and a second jaw 830. Either of first jaw 820 and second jaw 830 can be straight, round, or curved. First jaw 820 includes a staple cartridge 822 having a plurality of staples 824. Second jaw 830 may be in the form of an anvil defining a plurality of staple forming pockets 832 corresponding to the plurality of staples 824 of staple cartridge 822.

Referring now to FIG. 18A, each of staples 824 has a first leg 824a and a second leg 824b. Staple formation circuit 810 may be at least partially disposed on second jaw 830. As discussed in greater detail below, second jaw 830 may include a thin electrically resistive material (e.g., any suitable polymer) that electrically isolates at least a portion of staple formation circuit 810. The electrically resistive material can be a conformal layer. Alternatively or additionally, the electrically resistive material may electrically isolate the entire staple formation circuit 810.

In operation, as illustrated in FIG. 18B, staple formation circuit 810 communicates a signal "S1" to a controller 840 coupled to staple formation circuit 810. Controller 840 monitors staple conditions "SC" of one or more of the plurality of staples 824 and facilitates the operation of surgical instrument 800, in particular, end effector 806. With continued reference to FIG. 18B, signal "S1" is representative of staple conditions "SC." Staple conditions "SC" include one or more of a formation, a malformation, and a nonformation of one or more of first leg 824a and second leg 824b of one or more of staples 824 within one or more of staple forming pockets 832. First and second legs 824a, 824b of one or more of staples 824 may be monitored by controller 840 independently of the other leg. In response to signal "S1", controller 840 communicates a second signal "S2" to surgical stapling apparatus 800 directing surgical stapling apparatus 800 to perform one or more operations. The one or more operations include one or more of preventing further staple formation, facilitating further staple formation, emitting a warning, and emitting an error feedback.

With reference to FIGS. 18A-20, staple formation circuit 810 includes one or both of a parallel circuit and a series circuit positioned along one or both of first and second jaws 820, 830. The parallel circuit and/or series circuit includes one or more electrical traces 812 disposed within one or more of staple forming pockets 832. Electrical traces 812 may be formed in a sequential array. Electrical traces 812 may be applied, printed, etched, electrolyzed, electron beamed, photolithographically positioned, sprayed and/or adhered onto the underlying electrically resistive material discussed above.

As illustrated in FIG. 18A, each trace 812 extends transversely across the staple forming pocket 832, but may be positioned at any suitable orientation relative to staple forming pocket 832. Staple formation circuit 810 may be a single, dual, or multiple wire isolated circuit. Second jaw 830 may be or act as a common ground when staple formation circuit 810 is a single wire isolated circuit. In particular, masked openings (not shown) may be defined in the electrically resistive material described above to facilitate electrical communication with second jaw 830 for grounding purposes.

Figure 18C:
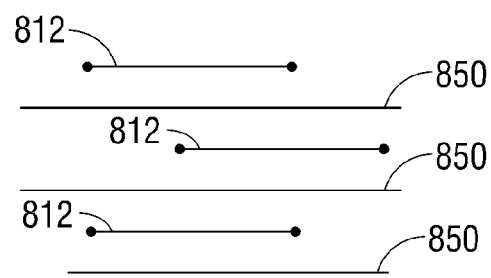
FIG. 18C is an illustrative view showing the relative positioning of layers of one embodiment of a staple formation circuit of the surgical stapling apparatus of FIG. 17.

Staple formation 810 circuit may include a plurality of electrical traces 812 positioned on second jaw or anvil 830 and associated with a respective staple forming pocket 832. To increase the number of electrical traces 812 for the limited geometry available on the surface of second jaw or anvil 830, a plurality of electrical traces 812 may be layered and separated by electrically resistive material 850 (e.g., any suitable polymer), as illustrated in FIG. 18C. In this regard, the plurality of electrical traces 812 can be applied over one another by electrically isolating them between additional alternating layers of electrically resistive material 850. Specifically, each electrical trace 812 may be electrically isolated from any of the other electrical traces 812. A final layer of electrically resistive material 850 can cover the top layer of electrical traces 812 to electrically isolate the entire circuit.

As best depicted in FIG. 18A, one or more electrical traces 812 may be positioned on a bottom surface of one of staple forming pockets 832 or any other suitable surface of staple forming pockets 832. One or more of staple forming pockets 832 may include a first recess 832*a* and a second recess 832*b*. An electrical trace 812 may be positioned within each recess 832*a*, 832*b* or within select recesses. Each electrical trace 812 may be operably coupled (relative to the parallel and/or series circuit) to one or more of a resistor, an inductor, a capacitor, a Piezo-Electric Crystal, a transducer (not shown) and/or any other electrical device known in the art suitable to facilitate the electrical communication between electrical traces 812 and controller 840 and enhance the feedback signal.

In use, at least one of first and second legs 824*a*, 824*b* of a staple 824 interrupts one of electrical traces 812 as staple 824 is formed in one of staple forming pockets 832. In this regard, the interruption of electrical trace 812 commences the communication of signal "S1" to controller 840. First and second legs 824*a*, 824*b* of one of staples 824 may be driven into electrical traces 812 with enough force to break electrical traces 812 to facilitate the communication of signal "S1." In accordance with the present disclosure, the proper formation of staple 824 results in electrical trace 812 being severed.

Turning now to FIGS. 19-22, end effector 806 may include one or more position indicating features 860 that track movement progression of one or more movable features 870 as the one or more movable features translate between proximal and distal positions. One or more position indicating features 860 include one or more of an encoder, a micro-switch, a magnetic transducer, a displacement transducer or any other suitable electrical, mechanical, and/or chemical device suitable to communicate a signal indicative of the positioning of one of movable features 870 during operation of surgical instrument 800, e.g., during formation progression of staples 824. One or more position indicating features 860 are operably coupled to controller 840, e.g., via one or more electrical traces 862 which may include any suitable electrically conductive material (e.g., copper) and any suitable dielectric insulation (e.g., polymer). One or more movable features 870 include a sled 872, a pusher 874, a knife 876, etc. One or more movable features 870 are movably positionable along one or both of jaws 820, 830 of end effector 806.

Figure 22:
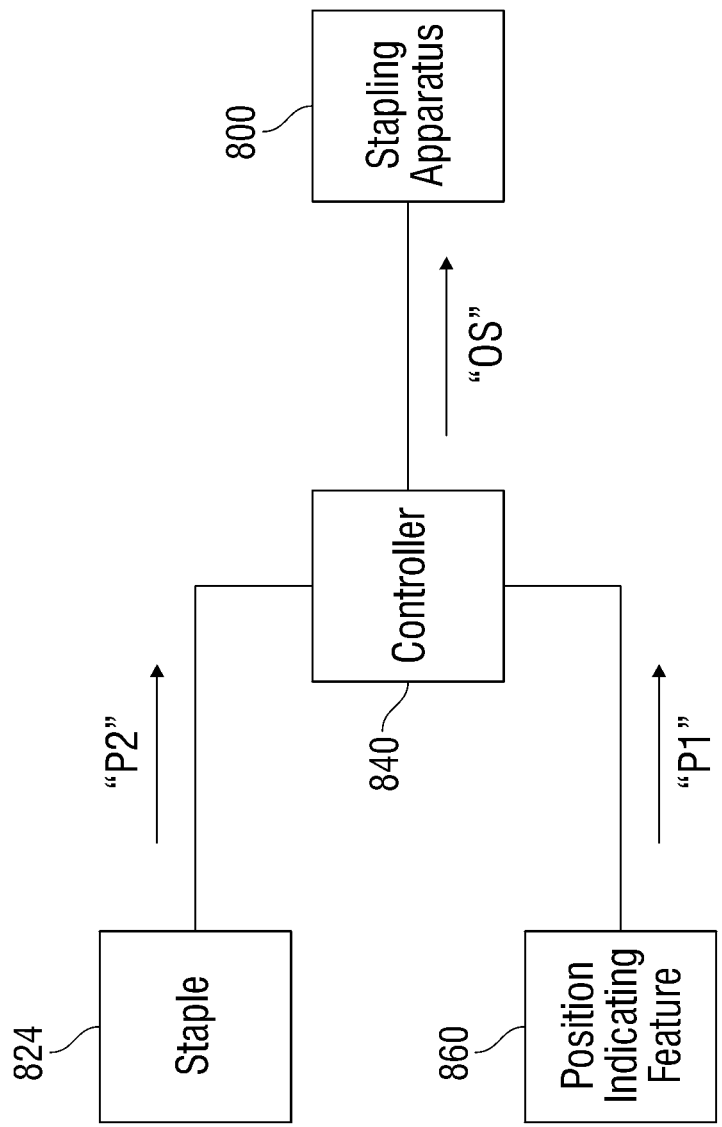
FIG. 22 is a block diagram illustrating the operation of the position indicating feature of FIG. 21.

As best depicted in FIG. 22, one or more position indicating features 860 communicate a first positioning signal "P1" to controller 840. First positioning signal "P1" represents the position of one or more movable features 870 as one or more movable features 870 move along one or both of jaws 820, 830 of end effector 806. Each staple 824 communicates a second positioning signal "P2" to controller 840 upon formation of staple 824. Second positioning signal "P2" represents the position of formed staple 824. Controller 840 compares the relative positions of formed staple 824 and one or more movable features 870 based upon first and second positioning signals "P1" and "P2." Upon comparison, controller 840 communicates an output signal "OS" to surgical stapling apparatus 800 directing surgical stapling apparatus 800 to perform one or more operations. The one or more operations include one or more of preventing further staple formation, facilitating further staple formation, emitting a warning, and emitting an error feedback.

Figure 21:
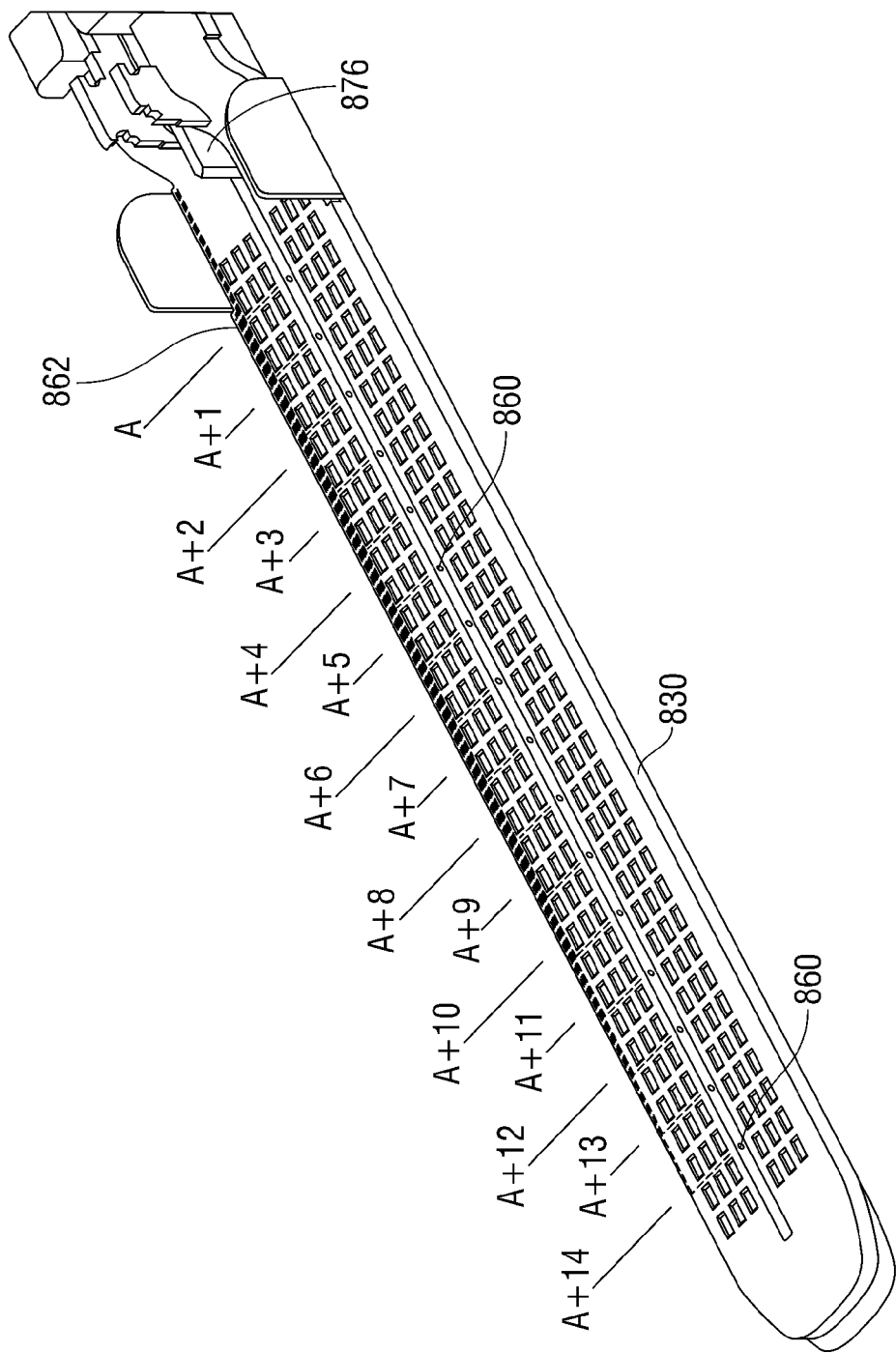
FIG. 21 is an enlarged, bottom perspective view of one embodiment of an anvil of the surgical stapling apparatus of FIG. 17, the anvil including a position indicating feature.

More specifically, one or more position indicating features 860 are positioned on surgical instrument (e.g., first jaw 820, second jaw 830 or any other suitable location on end effector 806) in sequential order for determining progression status and providing progression status feedback. As best shown in FIG. 21, t positioning indicating features 860 may be positioned for linear displacement (e.g., proximally/distally, laterally, transverse, etc.) or for angular displacement (e.g., circular) in sequential positions (e.g., A, A+1, A+2, . . . . . A+N), to monitor the position of one or more movable features 870 as one or more movable features 870 translate relative to end effector 806. For example, FIG. 21 illustrates a plurality of position indicating features 860 disposed along a knife channel 834 defined within second jaw 830. In this respect, the plurality of position indicting features 860 monitor the sequential positioning of knife 876 as knife 876 extends through second jaw 830.

Figure 19:
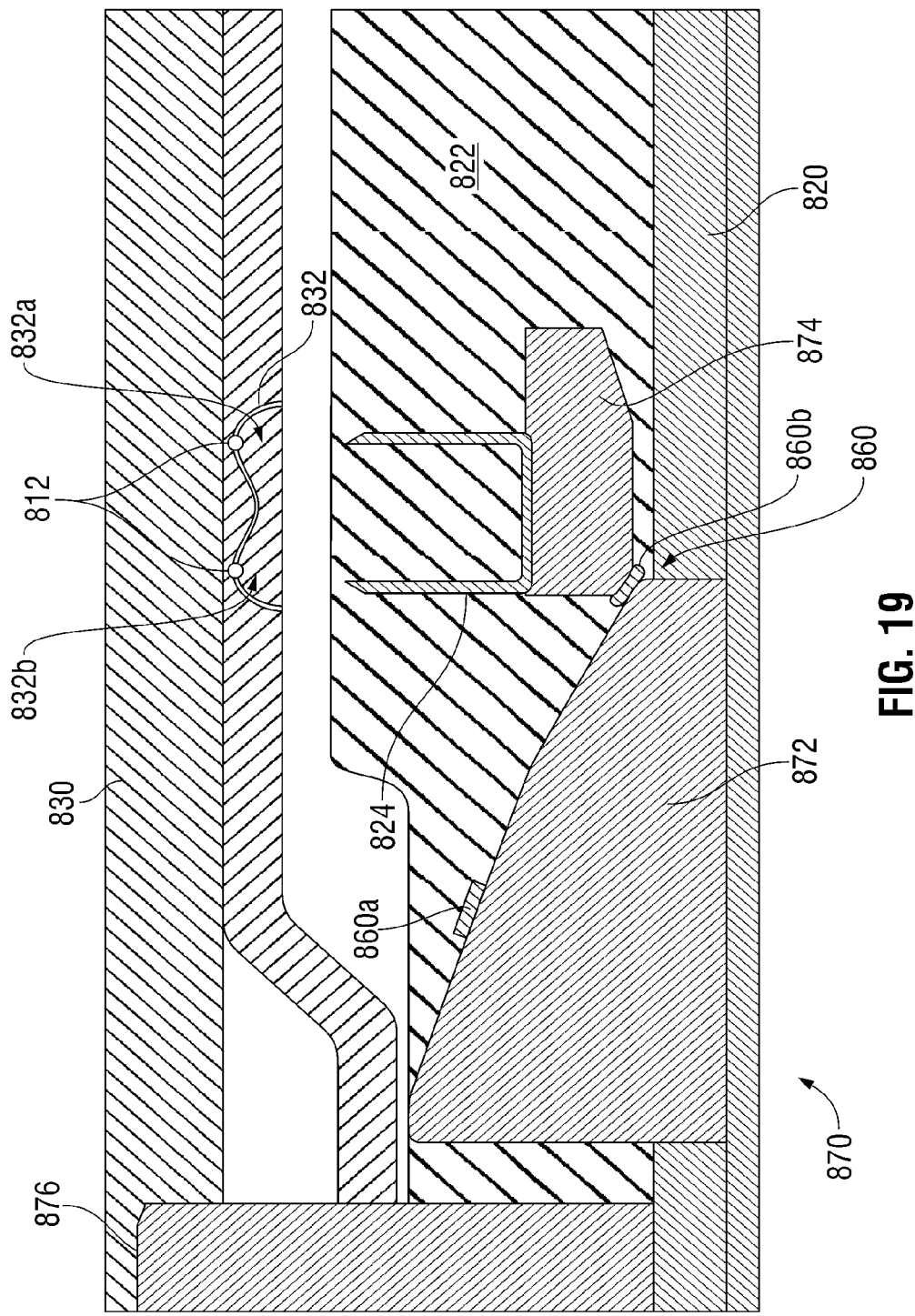
FIG. 19 is an enlarged, cross-sectional view of a portion of one embodiment of an end effector of the surgical stapling apparatus of FIG. 17 with components of the end effector being shown in a first position.
Figure 20:
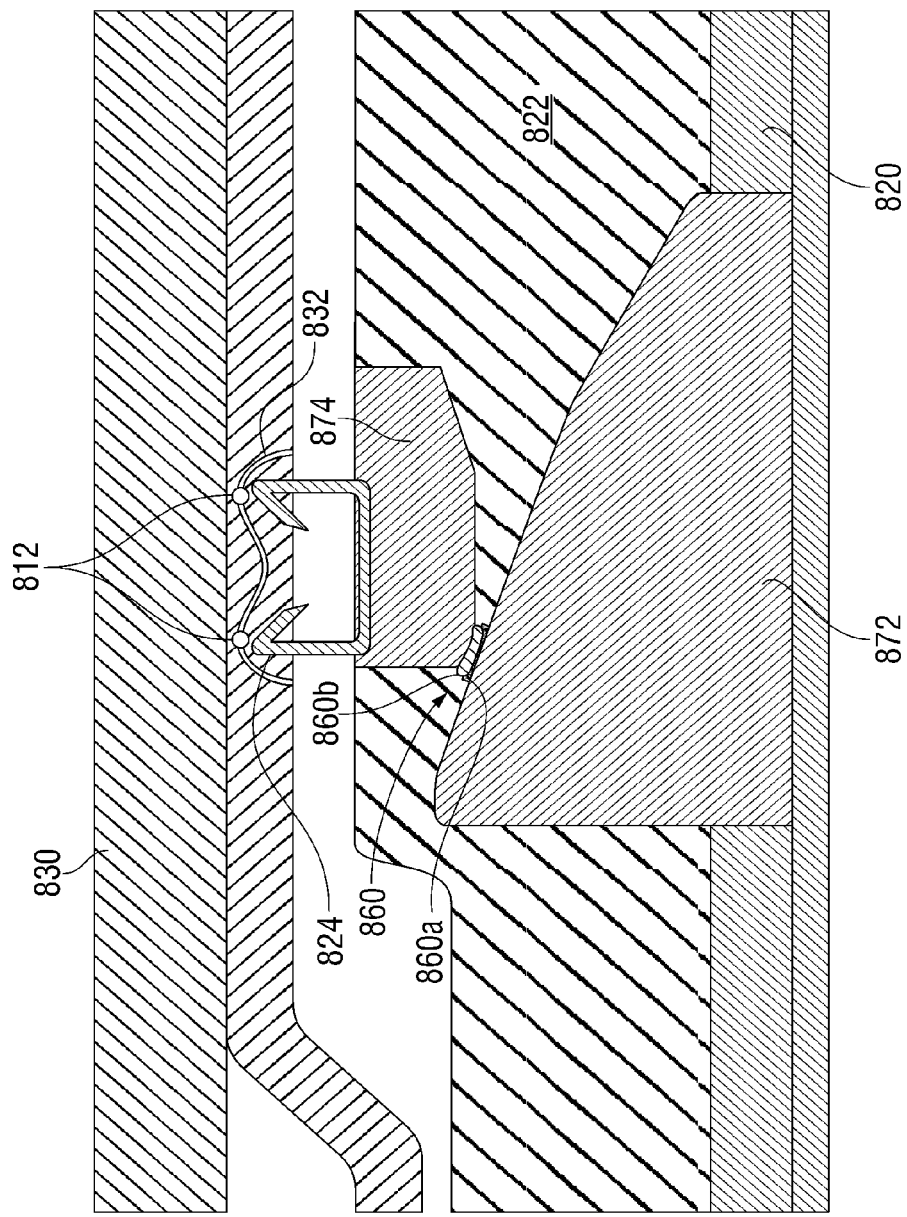
FIG. 20 is an enlarged, cross-sectional view of a portion of one embodiment of an end effector of the surgical stapling apparatus of FIG. 17 with components of the end effector being shown in a second position.

As illustrated in FIGS. 19-20, position indicating features 860 may include a first contact 860*a* and one or more second contacts 860*b*. First contact 860*a* is positioned on one of movable features 870 such as sled 872 and one or more second contacts 860*b* are positioned on one or more of pushers 874. In this regard, as sled 872 translates longitudinally from proximal to distal positions, first contact 860*a* of sled 872 engages one of the one or more second contacts 860*b* on one or more of pushers 874. The contact between first and second contacts 860*a*, 860*b*, as seen in FIG. 20, sends first positioning signal "P1" to controller 840.

Figure 23:
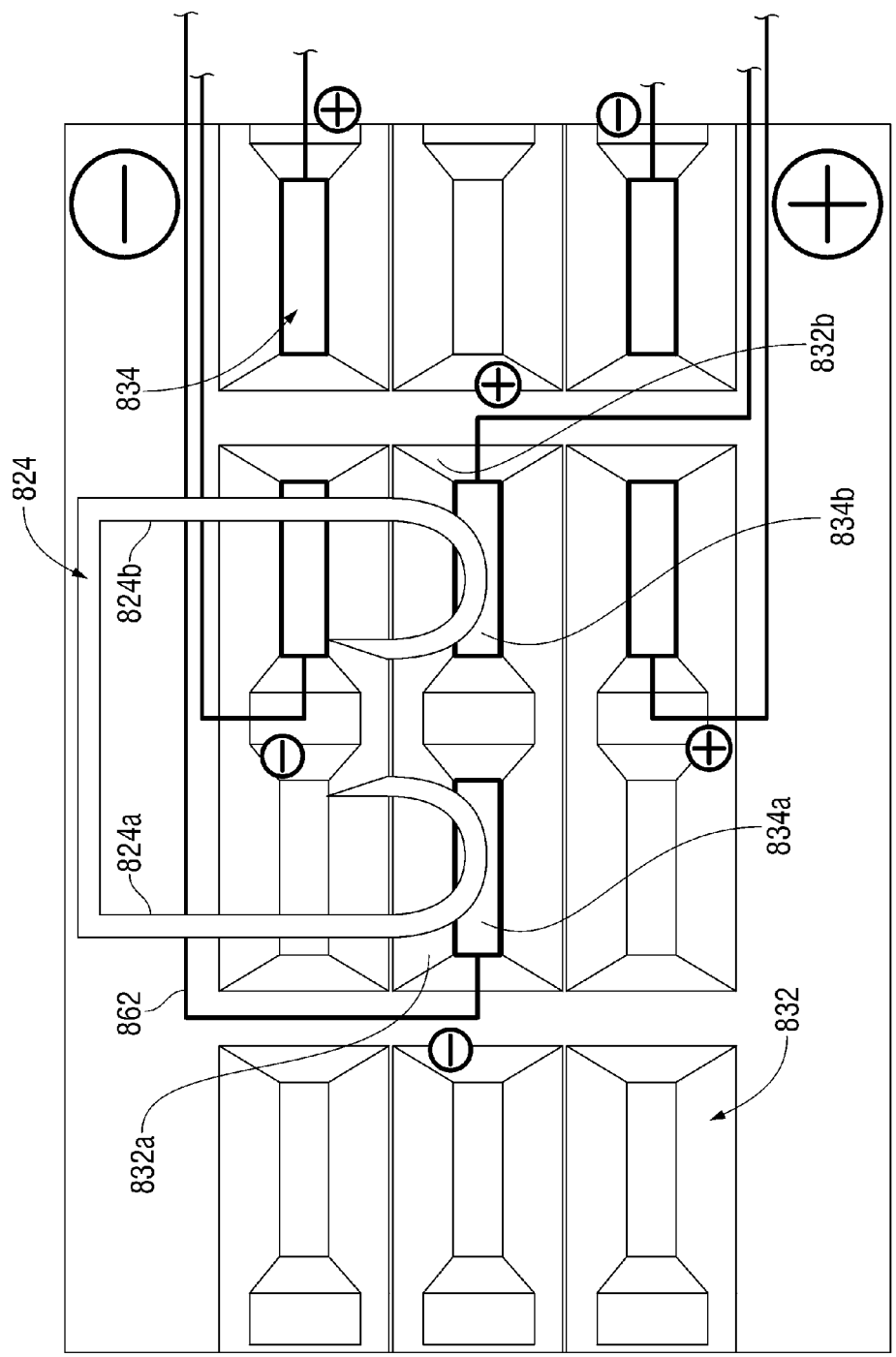
FIG. 23 is an enlarged, top view of a portion of one embodiment of an anvil of the surgical stapling apparatus of FIG. 17 with a staple being shown formed in a staple forming pocket of the anvil.

According to one embodiment, depicted in FIG. 23, one or more of staple forming pockets 832 may include one or more conductive pads 834 in electrical communication with staple formation circuit 810 (e.g., via electrical traces 862, each of which may be a positive or a negative electrical connection) to provide a conductive formation recognition circuit. In particular, a conductive pad 834 may be positioned in one or both recesses 832*a*, 832*b* of a staple forming pocket 832. In this regard, one or more conductive pads 834 form an open loop circuit in staple formation circuit 810 such that staple 824, upon formation, closes the open loop circuit, forming a closed loop circuit to conductively link the circuit and to provide an electrical signal of formation of staple 824 to controller 840 so that controller 840 can monitor and/or recognize staple condition "SC", e.g., formation, nonformation, and/or nonformation. As shown in FIG. 23, a first conductive pad 834*a* is positioned in first recess 832*a* and a second conductive pad 834*b* is positioned in second recess 832*b*. Thus, first leg 824*a* of staple 824 contacts conductive pad 834*a* and second leg 824*b* of staple 824 contacts conductive pad 834*b*, completing the circuit and allowing electricity to flow through the circuit. The closing of the circuit indicates to controller 840 that formation of staple 824 has been completed. The impedance/resistance of the completed circuit can be measured and qualified by controller 840 to properly determine the formation quality of each staple 824. In addition, the tips of legs 824*a*, 824*b* may be coated with an electrically resistive material to ensure that staple 824 is fully formed before conductively linking the circuit. In this respect, the tips of legs 824*a*, 824*b* are bent upwards and away from conductive pads 834*a*, 834*b* so that the portion of legs 824*a*, 824*b*, proximal the tips, contacts conductive pads 834*a*, 834*b* to permit electrical conductivity therethrough when staple 824 is substantially positioned in the desired "B" shape.

While several illustrative embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical stapling apparatus, comprising:
    an end effector having a first jaw and a second jaw, the first jaw having a staple cartridge with staples disposed therein and the second jaw having a plurality of staple forming pockets, the staple forming pockets including a first recess and a second recess;
    a staple formation circuit including traces formed on the second jaw, the traces being positioned in each of the first recess and the second recess of at least one of the staple forming pockets; and
    a controller electrically connected to the traces wherein the traces form a circuit, the formation of staples interrupt an electrical signal in one or more of the traces.

2. The surgical stapling apparatus according to claim 1, wherein the traces are positioned in a plurality of the staple forming pockets.

3. The surgical stapling apparatus according to claim 1, wherein at least some of the traces are formed in a layered fashion, with an electrically resistive material separating the layered traces.

4. The surgical stapling apparatus according to claim 1, further comprising one or more position indicating features to track the movement of a movable member.

5. The surgical stapling apparatus according to claim 4, wherein the movable member is a staple actuating sled.

6. The surgical stapling apparatus according to claim 5, wherein the staples are supported on pushers.

7. The surgical stapling apparatus according to claim 6, wherein the pushers have a position indicating feature associated therewith.

8. The surgical stapling apparatus according to claim 4, further comprising a knife for severing tissue between the first jaw and second jaw.

9. The surgical stapling apparatus according to claim 8, wherein the knife has a position indicating feature associated therewith.

10. The surgical stapling apparatus according to claim 4, wherein the position indicating feature is selected from the group consisting of an encoder, a micro-switch, a magnetic transducer, and a displacement transducer.

11. The surgical stapling apparatus according to claim 4, wherein at least one of the first jaw and the second jaw have a position indicating feature associated therewith.

12. The surgical stapling apparatus according to claim 11, wherein the position indicating features is a first contact and one or more second contacts.

13. The surgical stapling apparatus according to claim 1, wherein the staple cartridge has at least one first segment and at least one second segment.

14. The surgical stapling apparatus according to claim 13, further comprising a biasing member for each of the at least one first segment and at least one second segment.

15. The surgical stapling apparatus according to claim 14, further comprising a pressure sensor for each of the at least one first segment and at least one second segment.

16. The surgical stapling apparatus according to claim 1, further comprising a motor.

17. The surgical stapling apparatus according to claim 16, wherein the motor is disposed in a housing.

18. The surgical stapling apparatus according to claim 17, further comprising a power source in the housing and operatively connected to the motor.

19. The surgical stapling apparatus according to claim 1, wherein the staples are disposed in the staple cartridge in linear rows.

* * * * *

UNITED STATES PATENT AND TRADEMARK OFFICE
CERTIFICATE OF CORRECTION

| | | |
|---|---|---|
| PATENT NO. | : 9,782,170 B2 | Page 1 of 1 |
| APPLICATION NO. | : 14/598684 | |
| DATED | : October 10, 2017 | |
| INVENTOR(S) | : Zemlock et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 443 days.

Signed and Sealed this
Nineteenth Day of June, 2018

Andrei Iancu
*Director of the United States Patent and Trademark Office*